(12) United States Patent
Dervieux et al.

(10) Patent No.: US 7,563,590 B2
(45) Date of Patent: Jul. 21, 2009

(54) METHODS OF QUANTIFYING METHOTREXATE METABOLITES

(75) Inventors: Thierry Dervieux, San Diego, CA (US); Russell B. Richerson, Tucson, AZ (US)

(73) Assignee: Cypress Bioscience Inc., San Diego, CA (US)

( * ) Notice: Subject to any disclaimer, the term of this patent is extended or adjusted under 35 U.S.C. 154(b) by 363 days.

(21) Appl. No.: 10/232,760

(22) Filed: Aug. 30, 2002

(65) Prior Publication Data

US 2004/0043441 A1 Mar. 4, 2004

(51) Int. Cl.
*C12Q 1/34* (2006.01)
(52) U.S. Cl. .................................... 435/18
(58) Field of Classification Search .............. 435/7, 435/72, 18, 110, 147, 212; 544/81
See application file for complete search history.

(56) References Cited

U.S. PATENT DOCUMENTS

| | | | |
|---|---|---|---|
| 5,698,556 A | 12/1997 | Chan | 514/249 |
| 5,912,251 A | 6/1999 | Nair | 514/266.4 |
| 6,921,667 B2 * | 7/2005 | Dervieux et al. | 436/63 |
| 2004/0043441 A1 | 3/2004 | Dervieux et al. | |

OTHER PUBLICATIONS

Kinahan et al. "Fluorometric high-performance liquid chromatographic analysis of 10-deaazaaminopterin, 10-ethyl-deazaaminopterin, and known metabolites," Anal. Biochem. (1985) 150(1): 203-213.*
Chatterji et al. "Thermal and photolytic decomposition of Methotrexate in aqueous solutions" J. Pharmaceutical Sci. (1978) 67(4): 526-531.*
Goli et al. "Investigation of the conjugase treatment procedure in the microbiological assay of folate" Food Chem. (1992) 43: 57-64.*
Kubo et al. "Fluorometric determination of methotrexate in serum by high-perferance liquid chromatography using in-line oxidation with hydrogen peroxide" Anal. Sci. (1992) 8: 789-792.*
Suzuki et al. "Microanalysis of methotrexate . . . " Fresenius J. Anal. Chem. (1995) 351: 806-807.*
Longo et al., "γ-Glutamyl Hydrolase and Folylpolyglutamate Synthetase Activities Predict Polyglutamylation of Methotraxate in Acute Leukemias," Oncology Research 9:259-263 (1997).

Waltham et al., "Capillary electrophoresis of methotrexate polyglutamates and its application in evaluation of γ-glutamyl hydrolase activity," J. Chromatography B. 689:387-392 (1997).
Weigand et al., "Comparative analysis of methotrexate polyglutamates in lymphoblast preparations from bone marrow and blood, and the contribution of residual red blood cells," J. Cancer Res. Clin. Oncol. 126:407-411 (2000).
Angelis-Stoforidis et al., "Methotrexate polyglutamate levels in circulating erythrocytes and polymorphs correlate with clinical efficacy in rheumatoid arthritis," Clin. Exp. Rheumatology 17:313-320 (1999).
Alarcón, "Methotrexate use in rheumatoid arthritis. A clinician's perspective," Immunopharm. 47:259-271 (2000).
Chaykovsky, "Direct $N^8$-Alkylation of 2,4-Diamino-7,8-dihydropteridines. Preparation of 7,8-Dihydro-8-methylmethotrexate[1]" J. Org. Chem. 40:145-146 (1975).
Dervieux et al., "De novo purine synthesis inhibition and antileukemic effects of mercaptopurine alone or in combination with methotrexate in vivo," Blood 100:1240-1247 (2002).
Endresen and Husby, "Folate supplementation during methotrexate treatment of patients with rheumatoid arthritis," Scand. J. Rheumatol. 30:129-134 (2001).
Esaki et al., "Organization and structure of the mouse Y-glutamyl hydrolase gene and the functional identification of its promoter," Gene 234:93-100 (1999).
Frei et al., "Clinical studies of dichloromethotrexate (NSC 29630)" Clin. Pharmacol. Therap. 6:160-171 (1965).
Galpin et al., "Differences in Folypolyglutamate Synthetase and Dihydrofolate Reductase Expression in Human B-Lineage versus T-Lineage Leukemic Lymphoblasts: Mechanisms for Lineage Differences in Methotrexate Polyglutamylation and Cytotoxicity," Mol. Pharm. 52:155-163 (1997).
Giverhaug et al., "The interaction of 6-mercaptopurine (6-MP) and methotrexate (MTX)," General Pharm. 33:341-346 (1999).
Henkin and Washtien, "Novel Fluorinated Antifolates. Enzyme Inhibition and Cytotoxicity Studies on 2'- and 3'-Fluoroaminopterin," J. Med. Chem. 26:1193-1196 (1983).
Imbert et al., "Enzymatic Assay for Methotrexate with a Centrifugal Analyzer (Cobas-Bio)," Clin. Chem. JID 29:1317-1318 (1983).

(Continued)

*Primary Examiner*—Michael G Wityshyn
*Assistant Examiner*—Susan Hanley
(74) *Attorney, Agent, or Firm*—Cooley Godward & Kronish LI

(57) ABSTRACT

The present invention provides a method for efficiently converting methotrexate polyglutamates to methotrexate in a cellular extract by contacting the cellular extract with gamma glutamyl hydrolase under conditions suitable for efficient conversion of methotrexate polyglutamates to methotrexate.

32 Claims, 7 Drawing Sheets

OTHER PUBLICATIONS

Jolivet and Chabner, "Intracellular Pharmacokinetics of Methotrexate Polyglutamates in Human Breast Cancer Cells; Selective Retention And Less Dissociable Binding of 4-$NH_2$-10-$CH_3$-Pteroylglutamate$_4$ and 4-$NH_2$-10-$CH_3$-Pteroylglutamate$_5$ To Dihydrofolate Reductase," *J. Clin. Invest.* 72:773-778 (1983).

Kamen, "Folate and Antifolate Pharmacology," *Semin. Oncol.* 24:S18-30 to S18-39 (1997).

Kamen and Winick, "Analysis of Methotrexate Polyglutamate Derivatives in Vivo," *Meth. Enz.* 122:339-346 (1986).

Krakower et al., "Separation and Identification of Subpicomole Amounts of Methotrexate Polyglutamates in Animal and Human Biopsy Material," *Analytical Biochem.* 122:412-416 (1982).

Longo-Sorbello and Bertino, "Current understanding of methotrexate pharmacology and efficacy in acute leukemias. Use of newer antifolates in clinical trials," *Haematolgica* 86:121-127 (2001).

Lucock et al., "Analysis and Biochemistry of Blood Folate," *Biochem. Mol. Med. JID* 58:93-112 (1996).

McGown et al., "Results with Commercial Radioassay Kits Compared with Microbiological Assay of Folate in Serum and Whole-Blood," *Clin. Chem.* 24:2186-2191 (1978).

Ndaw et al., "Determination of folates in foods by high-performance liquid chromatography with fluorescence detection after precolumn conversion to 5-methyltetrahydrofolates," *Journal of Chromatography* 928:77-90 (2001).

Pfeiffer and Gregory, "Enzymatic deconjugation of erythrocyte polyglutamyl folates during preparation for folate assay: investigation with reversed-phase liquid chromatography," *Clinical Chemistry* 42:1847-1854 (1996).

Pizzorno et al., "Multifactorial Resistance to 5,10-Dideazatetrahydrofolic Acid in Cell Lines Derived from Human Lymphoblastic Leukemia CCRF-CEM," *Cancer Res.* 55:566-573 (1995).

Rhee et al., "Characterization of Human Cellular Y-Glutamyl Hydrolase," *Mol. Pharmacol.* 53:1040-1046 (1998).

Rosowsky and Chen, "Methotrexate Analogs. 4,7-Methyl Derivatives of Methotrexate and Dichloromethotrexate. A New Synthesis and Some Biological Studies," *J. Med. Chem.* 17:1308-1311 (1974).

Rubino, F., "Separation methods for methotrexate, its structural analogues and metabolites," *J. Chromatoq.* 764:217-254 (2001).

Šalamoun and František, "Determination of Methotrexate And Its Metabolites 7-Hydroxymethotrexate and 2,4-Diamino-$N^{10}$-Methylpteroic Acid In Biological Fluids By Liquid Chromatography With Fluorimetric Detection," *Journal of Chromatography* 378:173-181 (1986).

Šalamoun et al., "Column Liquid Chromatography Of Methotrexate And Its Metabolites Using A Post-Column Photochemical Reactor And Fluorescence Detection," *Journal of Chromatography* 419:213-223 (1987).

Sato, "Methotrexate therapy in sytemic lupus erythematosus," *Lupus* 10:162-164 (2001).

Schrøder and Heinsvig, "Enzymatic assay for methotrexate in erythrocytes," *Scand. J. Clin. Lab. Invest.* 45:657-659 (1985).

Tomcufcik and Seeger, "The Synthesis of the 3'-Fluoro and 3',5'-Difluoro Derivatives of 4-Amino-4-deoxy-$N^{10}$-methylpteroylglutamic Acid (Methotrexate)," *J. Organic Chem.* 26:3351 (1961).

Widemann et al., "Dihydrofolate Reductase Enzyme Inhibition Assay for Plasma Methotrexate Determination Using a 96-Well Microplate Reader," *Clin. Chemistry* 45:223-228 (1999).

Widemann et al., "Pharmacokinetics and Metabolism of the Methotrexate Metabolite 2,4-Diamino-$N^{10}$-methylpteroic Acid," *J. Pharmacol. Exp. Ther.* 294:894-901 (2000).

Yao et al., "Human Y-glutamyl hydrolase: Cloning and characterization of the enzyme expressed in vitro," *Proc. Natl. Acad. Sci. USA* 93:10134-10138 (1996).

Yao et al., "Identification, Cloning, and Sequencing of a cDNA Coding for Rat Y-Glutamyl Hydrolase," *J. Biol. Chem.*, 271:8525-8528 (1996).

Anzai et al. "Separation and Identification of Methotrexate and its Metabolites, 7-Hydroxymethotrexate and Polyglutamates, in Human Tissues by Reversed-Phased High-Performance Liquid Chromatography Coupled with Radioimmunoassay," *Journal of Chromatography*, 1987, vol. 415, pp. 445-449.

Dervieux et al. "Effect of Methotrexate Polyglutamates on Thioguanine Nucleotide Concentrations During Continuation Therapy of Acute Lymphoblastic Leukemia with Mercaptopurine," *Leukemia*, 2006, vol. 16, pp. 209-212.

Dervieux et al. "HPLC Determination of Erythrocyte Methotrexate Polyglutamates after Low-Dose Methotrexate Therapy in Patients with Rheumatoid Arthritis," *Clinical Chemistry*, 2003, vol. 49, No. 10, pp. 1632-1641.

Masson et al. "Accumulation of Methotrexate Polyglutamates in Lumphoblasts Is a Determinant of Antileukemic Effect in Vivo," *Journal of Clinical Investigation*, Jan. 1996, vol. 1, pp. 73-80.

Muindi et al. "Specific and Sensitive High-Performance Liquid Chromatographic Method with Fluorescence Detection for Measurement of Lometrexol and its Polyglutamates in Biologic Samples," *Journal of Chromatography*, 1993, vol. 621, pp. 55-64.

Sczesny et al. "Capillary Electrophoretic Drug Monitoring of Methotrexate and Leucovorin and Their Metabolites," *Journal of Chromatography*, 1998, vol. 718, pp. 177-185.

Synoid et al. "Blast Cell Methotrexate-Polyglutamate Accumulation in Vivo Differs by Lineage, Ploidy, and Methotrexate Dose in Acute Lymphoblastic Leukemia," *Journal of Clinical Investigation*, Nov. 1994, vol. 94, pp. 1996-2001.

Dervieux, et al.; "Effect of methotrexate polyglutamates on thioguanine nucleotide concentrations during continuation therapy of acute lymphoblastic leukemia with mercaptopurine;" *Leukemia*; 16, 209-212 (2002).

Hendel et al.; "Pharmacokinetics of Methotrexate in Erythrocytes in Psoriasis;" *European Journal of Clinical Pharmacology*; 27: 607-610; (1984).

Kamen, et al.; "Methotrexate Accumulation and Folate Depletion in Cells as a Possible Mechanism of Chronic Toxicity to the Drug;" *British Journal of Haematology*; 49, 355-360 (1981).

Lena et al.; "Kinetics of Methotrexate and its Metabolites in Red Blood Cells;" *Cancer Drug Delivery*; vol. 4, No. 2: 119-127; (1987).

Schmiegelow et al.; "Myelotoxicity, Pharmacokinetics, and Relapse Rate with Methotrexate/6-Mercaptopurine Maintenance Therapy of Childhood Acute Lymphoblastic Leukemia;" *Pediatric Hematology and Oncology*; 13:433-441; (1996).

Schroder, et al.; "Methotrexate and its polyglutamate derivatives in erythrocytes during and after weekly low-dose oral methotrextae therapy of children with acute lymphoblastic leukemia;" *Cancer Chemother Pharmacol*; 21: 145-149; (1988).

Schroder, et al.; "In vivo decline of methotrexate and methotrexate polyglutamates in age-fractionated erythrocytes;" *Cancer Chemother Pharmacol*; 21: 150-155; (1988).

T. Dervieux; Polyglutamation of Methotrexate With Common Polymorphisms in Reduced Folate Carrier, Aminoimidazole Carboxamide Ribonucleotide Transformylase, and Thymidylate Synthase are Associated With Methotrexate Effects in Rheumatoid Arthritis; *Arthritis & Rheumatism*; vol. 50, No. 9, previously presented 2766-2774 (2004).

T. Dervieux et al; Contribution of common polymorphisms in reduced folate carrier and γ-glutamylhydrolase to methotrexate polyglutamate leve3Is in patients with rheumatoid arthritis; *Pharmacogenetics*; 14:733-739 (2004).

Belkov et al.; Reduced Folate Carrier Expression in Acute Lymphoblastic Leukemia: A Mechanism for Ploidy but not Lineage Differences in Methotrexate Accumulation; *Blood*; vol. 93, No. 5; previously presented 1643-1650 (1999).

Y. Berkun, et al.; Methotrexate related adverse effects in patients with pheumatoid arthritis are associated with the A1298C polymorphism of the MTHFR gene; *Ann Rhem Dis*; 63:1227-1231 (2004).

C. Skibola, et al.; Polymorphisms in the thymidylate synthase and serine hydroxymethyltransferase genes and risk of adult acute lymphocytic leukemia; *Blood*; vol. 99, No. 10: 3786-3791; (2002).

K. Chave, et al.; Identification of single nucleotide polymorphisms in the human γ-glutamyl hydrolase gene and characterization of promoter polymorphisms; *Gene*; 319: 167-175; (2003).

J. Ma et al.; A Polymorphism of the Methionine Synthase Gene: Association with Plasma Folate, Vitamin B12, Homocyst(e)ine, and Colorectal Cancer Risk; *Cancer Epidemiology, Biomarkers and Prevention*; vol. 8, 825-829 (1999).

A. Ulvik et al.; Single Nucleotide Polymorphism (SNP) Genotyping in Unprocessed WShole Blood and Serum by Real-Time PCR: Application to SNPs Affecting Homocysteine and Folate Metabolism; *Clinical Chemistry*; vol. 47, 2050-2053; (2001).

Brouwer et al. "Analysis of Methotrexate and MTX-Polyglutamates Using Affinity/HPLC with Post-Column Derivatization," Faseb Journal, Mar. 2000, vol. 14, No. 4, p. A720.

Cole Peter D. et al., "Effects of Overexpression of Gamma-Glutamyl Hydrolase on Methotrexate Metabolism and Resistance." Cancer Research, vol. 61, No. 11, Jun. 1, 2001, pp. 4599-4604.

Panetta John Carl et al., "Methotrexate Intracellular Disposition in Acute Lymphoblastic Leukemia: a Mathematical Model of Gamma-Glutamyl Hydrolase Activity." Clinical Cancer Research, vol. 8, No. 7, Jul. 2002, pp. 2423-2429.

Supplementary European Search Report, EP Application No. 03 75 1939.4-2405, based on PCT/US0327313, dated Nov. 28, 2008.

* cited by examiner

Methotrexate

Methotrexate polyglutamates

A

B

METHODS OF QUANTIFYING METHOTREXATE METABOLITES

BACKGROUND OF THE INVENTION

This invention relates generally to methods for monitoring drug therapy and, more specifically, to methods for monitoring efficacy and toxicity of anti-folate drug therapy.

Folate (folic acid) is a vitamin that is essential for the life-sustaining processes of DNA synthesis, replication and repair. Folate is also important for protein biosynthesis, another process that is central to cell viability. The pteridine compound, methotrexate (MTX), is structurally similar to folate and as a result can bind to the active sites of a number of enzymes that normally use folate as a coenzyme for the biosynthesis of the purine and pyrimidine nucleotide precursors of DNA and for the interconversion of amino acids during protein biosynthesis. Despite its structural similarity to folic acid, MTX cannot be used as a cofactor by enzymes that require folate, and instead competes with the folate cofactor for enzyme binding sites, thereby inhibiting protein and DNA biosynthesis and, hence, cell division.

The ability of methotrexate to inhibit cell division has been exploited in the treatment of a number of diseases and conditions that are characterized by rapid or aberrant cell growth. As an example, autoimmune diseases are characterized by an inappropriate immune response directed against normal autologous (self) tissues and are mediated by rapidly replicating T-cells or B-cells. Autoimmune diseases that have been treated with MTX include, for example, multiple sclerosis, rheumatoid arthritis, psoriasis, the autoimmune stage of diabetes mellitus (juvenile-onset or Type 1 diabetes), autoimmune uveoretinitis, myasthenia gravis, autoimmune thyroiditis, and systemic lupus erythematosus.

Because many malignant cells proliferate more rapidly than normal cells, MTX can also be used to selectively impair cancerous cell growth. As a consequence, methotrexate is a widely used anticancer agent, employed, for example, in the treatment of acute lymphocytic leukemia, breast cancer, epidermoid cancers of the head and neck, advanced mycosis fungoides, lung cancer, non-Hodgkins lymphomas, gestational choriocarcinoma, chorioadenoma destruens, and hydatidiform moles.

Despite its therapeutic efficacy for a wide variety of diseases and conditions, treatment with methotrexate can present a risk to the patient. In particular, because MTX interferes with processes required for replication and division of normal as well as diseased cells, inappropriately high levels of the drug can lead to destruction of actively proliferating non-target tissues such as bone marrow and intestinal mucosa. MTX consequently is associated with renal and hepatic toxicity when administered in the "high-dose regimen" that is required for some conditions. In addition, low-dose MTX therapy can lead to toxicity and unwanted side-effects in some patients, where the dosage is not appropriate due to individual variability in pharmacokinetic parameters influencing, for example, drug uptake, targeting and clearance. This situation is especially problematic in the treatment of chronic conditions such as rheumatoid arthritis, where methotrexate can be administered over a period of many years.

Because individual differences in pharmacokinetic parameters can be difficult to predict, safe and effective methotrexate treatment strategies require that methotrexate or methotrexate metabolite levels be monitored in patients being treated. A variety of methods have been developed for monitoring MTX drug concentrations in plasma including bioassays, immunological detection and chromatographic assays. Such plasma detection methods have been useful for monitoring high dose MTX therapy in some clinical applications. However, these plasma detection methods have not been useful in monitoring low-dose methotrexate therapy.

Methotrexate is metabolized upon uptake by mammalian cells, such that one or more glutamyl moieties are added to MTX to yield a mixture of methotrexate polyglutamates (MTXPGs). The number of glutamyl moieties that can be added to MTX generally varies from two to seven. MTXPGs do not readily efflux from cells and thus are able to exert their cytotoxic effects over long periods of time. Levels of intracellular MTXPGs have been shown to be higher in patients that responded to MTX therapy as compared the intracellular levels in patients that did not respond. Currently available methods for measuring cellular MTXPG levels are based on a dihydrofolate reductase enzyme assay in which MTXPG levels are calculated based on inhibition of the dihydrofolate reductase enzyme. However, the extent of enzyme inhibition in these assays is dependent upon the number of glutamyl residues attached to MTX, rendering an accurate determination of intracellular MTXPGs levels impossible by this method. The variability of dihydrofolate reductase based assays can be further exacerbated in some situations because folates, which are present in different amounts depending upon an individual's response to MTX therapy and the amount of folate contributed by diet, also influence the results of the assay.

Thus, there exists a need for new methods for determining intracellular levels of methotrexate polyglutamates and for monitoring the efficacy and toxicity of methotrexate therapy such as low-dose methotrexate therapy. The present invention satisfies this need and provides related advantages as well.

SUMMARY OF THE INVENTION

The present invention provides a method for efficiently converting methotrexate polyglutamates (MTXPGs) to methotrexate (MTX) in a cellular extract by contacting the cellular extract with gamma glutamyl hydrolase under conditions suitable for efficient conversion of MTXPGs to MTX. The method is useful for quantitating the level of MTXPGs in a cellular extract.

The invention further provides a method for determining a level of methotrexate polyglutamates in a cellular extract. The method includes the steps of: (a) converting the MTXPGs to methotrexate in a cellular extract under conditions suitable for efficient conversion of MTXPGs to MTX, and (b) determining a level of the MTX, where the level of MTX can be correlated with the level of MTXPGs in the cellular extract.

The invention also provides a method for determining a level of methotrexate in a cellular extract by (a) irradiating the cellular extract, thereby producing a fluorescent MTX photolytic product; and (b) determining a level of the fluorescent MTX photolytic product, wherein the level of the fluorescent MTX photolytic product can be correlated with the level of MTX. By indirectly determining the intracellular level of methotrexate polyglutamates, a method of the invention can be useful, for example, for monitoring the efficacy or toxicity of MTX therapy.

The invention provides a method of optimizing therapeutic efficacy or reducing toxicity associated with methotrexate therapy administered to an individual. The method includes the steps of: (a) converting methotrexate polyglutamates to MTX in a cellular extract from an individual under conditions suitable for efficient conversion of MTXPGs to MTX; and (b) determining a level of MTX in the cellular extract, the level of MTX correlating with a level of MTXPGs, thereby determining a level of MTXPGs in the cellular extract, wherein a drug or dosage subsequently administered to the individual is selected based on the level of MTXPGs.

The invention further provides an isolated deglutamated composition which is characterized as (a) present in a red blood cell extract following deglutamation; (b) having a retention time of about 12 minutes in a mobile phase consisting of a 15-minute linear gradient from 2% acetonitrile/98% mobile phase A to 25% acetonitrile/75% mobile phase A at a flow rate of 1 ml/min through a Terra MS C18 reverse phase column, where the reverse phase column has dimensions of 25 cm×4.6 mm and a particle size of 5 micrometers and where the mobile phase A contains 10 mM ammonium acetate, pH 6.5, and 0.06% hydrogen peroxide in water; and (c) having a fluorescence excitation spectrum with peaks at 299 nm and 402 nm in water and a fluorescence emission spectra with a peak at 460 nm in water.

The deglutamated endogenous composition of the invention can be produced by: (a) converting polyglutamated compounds in a red blood cellular extract to produce deglutamated RBC compounds; (b) fractionating the deglutamated RBC compounds under conditions including passage of a mobile phase consisting of a 15-minute linear gradient from 2% acetonitrile/98% mobile phase A to 25% acetonitrile/75% mobile phase A at a flow rate of 1 ml/min through a Terra MS C18 reverse phase column, wherein the reverse phase column has dimensions of 25 cm×4.6 mm and a particle size of 5 micrometers and wherein the mobile phase A includes 10 mM ammonium acetate, pH 6.5 and 0.06% hydrogen peroxide in water; and (c) isolating a compound that elutes in a peak at 12 minutes, where the peak is detectable by emission at 464 nm upon excitation with radiation at 400 nm following photolysis of the compound by irradiation at 254 nm for 3 seconds in 80% mobile phase A/20% acetonitrile.

The deglutamated endogenous composition of the invention can combined, if desired, with a pharmaceutically acceptable carrier to produce a pharmaceutical composition. Such a pharmaceutical composition can be useful, for example, in a therapeutic method and can optionally include methotrexate. According to the invention, the deglutamated endogenous composition of the invention is also provided as a kit for use in a therapeutic or diagnostic method.

A deglutamated endogenous composition of the invention can be useful for reducing toxicity associated with methotrexate therapy. A deglutamated endogenous composition of the invention also can be useful in diagnostic methods such as methods for determining an intracellular level of methotrexate or a method of optimizing therapeutic efficacy or reducing toxicity associated with methotrexate therapy.

DETAILED DESCRIPTION OF THE INVENTION

Figure 1:
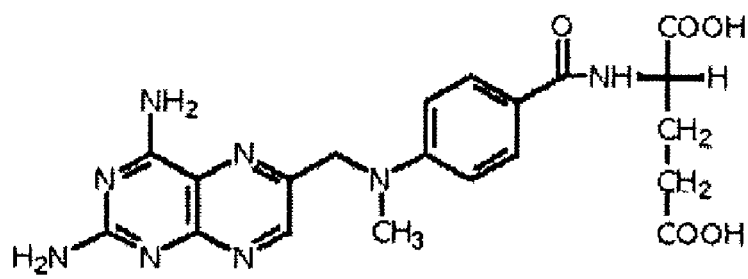
FIG. 1 shows the structures of methotrexate and methotrexate polyglutamates. (A) The chemical structure of methotrexate. (B) The chemical structure for methotrexate polyglutamate, where n refers to the number of glutamates attached to methotrexate.
Figure 1:
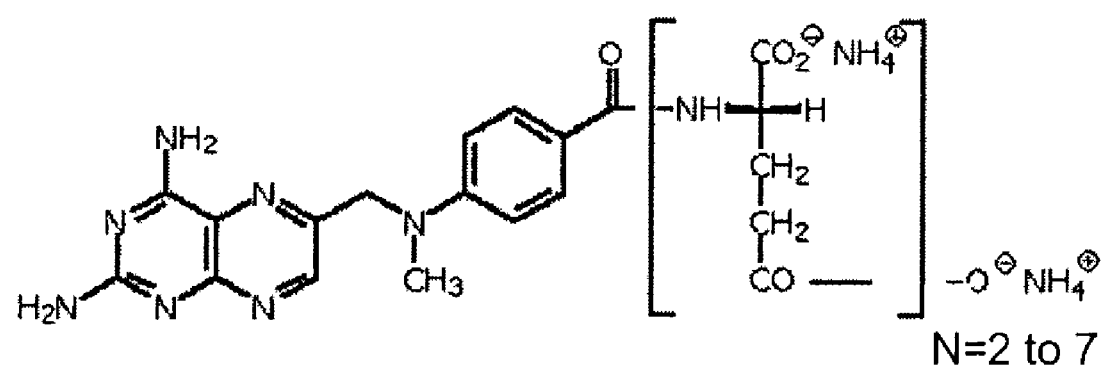

As disclosed herein, intracellular levels of methotrexate (MTX) were quantitated by fluorimetric detection of MTX photolytic products. As disclosed in Example I, a cell extract containing MTX was chromatographically separated and photolysed to yield MTX photolytic products which were of fluorimetrically detected. The method was demonstrated to detect MTX at low concentrations such as 5 nmol/L.

As further disclosed herein, methotrexate polyglutamates (MTXPGs) in a cellular extract were efficiently converted to MTX by contacting the extract with plasma as a source of gamma glutamyl hydrolase. Efficient conversion of intracellular MTXPGs to MTX, combined with fluorimetric detection of MTX photolytic products, allowed accurate quantitation of cellular MTXPG levels as demonstrated in Example II. As further disclosed in Example III, a method of the invention for quantitating cellular MTXPG levels was useful in monitoring intracellular MTXPG levels in patients undergoing low-dose MTX therapy. Thus, as disclosed herein, the methods of the invention can be useful, for example, for determining the percentage of MTX that has been metabolized to MTXPGs in a cellular extract. The methods of the invention also can be useful for quantitating cellular MTXPG levels in order to determine the efficacy or toxicity of methotrexate therapy.

The present invention further is directed to the discovery of an endogenous compound that is present in deglutamated red blood cell extracts. As demonstrated in Example IV, the endogenous compound can be chromatographically separated from unrelated red blood cell components. The endogenous compound is characterized by (a) being present in red blood cells following deglutamation; (b) having a retention time of about 12 minutes in a mobile phase consisting of a 15-minute linear gradient from 2% acetonitrile/98% mobile phase A to 25% acetonitrile/75% mobile phase A at a flow rate of 1 ml/min through a Terra MS C18 reverse phase column, which has dimensions of 25 cm×4.6 mm and a particle size of 5 micrometers, where mobile phase A contains 10 mM ammonium acetate, pH 6.5, and 0.06% hydrogen peroxide in water; and (c) having a fluorescence excitation spectrum with peaks at about 299 nm and 402 nm in water and fluorescence emission at about 464 nm in water. The endogenous compound can be, for example, photostable to UV light for at least 3 seconds and further can be selectively present in a deglutamated RBC extract but absent from an untreated RBC extract.

As further disclosed herein, detection or monitoring of the levels of the endogenous compound can be used to optimize therapeutic efficacy or reduce toxicity associated with methotrexate therapy. In particular, the levels of MTX and the endogenous deglutamated compound can be monitored and compared to optimize therapeutic efficacy or reduce toxicity associated with methotrexate or other anti-folate therapy. The endogenous compound also can function as an analog of folic acid and can be a useful adjunct to methotrexate therapy. As an example, the isolated endogenous compound can be administered to an individual undergoing methotrexate therapy in order to reduce attendant toxicity.

Based on these findings, the present invention provides a method for efficiently converting MTXPGs to MTX in a cellular extract by contacting the cellular extract with gamma glutamyl hydrolase under conditions suitable for efficient conversion of MTXPGs to MTX. A method of the invention can be useful, for example, for removing MTXPGs from a cellular extract, for isolating MTX from a cellular extract or for quantitating the level of MTXPGs in a cellular extract as described further below.

As used herein, the term "methotrexate" is synonymous with "MTX" and means a molecule having the structure shown in FIG. 1A. MTX includes, in part, a 2,4-diamino substituted pterine ring moiety linked at the 6 position to the amino group of a p-aminobenzoyl moiety, the p-aminobenzoyl moiety having a methylated amino group and being amide bonded to a glutamic acid moiety. Methotrexate functions as an inhibitor of dihydrofolate reductase (DHFR), decreasing the production of tetrahydrofolate (THF) from dihydrofolate (DHF). As a consequence, MTX indirectly inhibits purine and thymidine synthesis and amino acid interconversion. MTX also exhibits anti-proliferative activity through inhibition of thymidylate synthesis, which is required to synthesize DNA (Calvert, *Semin. Oncol.* 26:3-10 (1999)). MTX and its synthesis and properties are described in further detail in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; and 4,767,859. Methods of using MTX to treat cancer are described, for example, in U.S. Pat. Nos. 4,106,488, 4,558, 690, and 4,662,359.

Methotrexate, which is useful in the treatment of a variety of autoimmune diseases and cancers, is typically administered by the oral or parenteral route. MTX is readily distributed to body tissues, where it is transported into cells by a specific carrier system which includes components such as the reduced folate carrier, RCF1, and the folate receptor. Due to its high polarity at physiological pH, MTX does not readily pass through the cell membrane, and the majority of MTX enters cells via specific carriers. Once inside the cell, MTX is converted to MTXPGs by specific enzymes such as folylpoly-gamma-glutamate synthetase, which add one or more glutamic acid moieties, linked by iso-peptidic bonds to the γ-carboxyl of MTX as described, for example, in Kamen, *Semin. Oncol.* S18:30-39 (1997).

As used herein, the term "methotrexate polyglutamate" is synonymous with "MTXPG" and means a derivative of MTX having two or more glutamates which are amide bonded to the p-aminobenzoyl moiety of MTX as shown in the generalized structure of FIG. 1B. The number of glutamates in a methotrexate polyglutamate varies from two to seven or more; the number of glutamate moieties can be denoted by "n" using the nomenclature $MTXPG_n$ such that, for example, $MTXPG_2$ is MTXPG having two glutamates, $MTXPG_3$ is MTXPG having three glutamates, $MTXPG_4$ is MTXPG having four glutamates, $MTXPG_5$ is MTXPG having five glutamates, $MTXPG_6$ is MTXPG having six glutamates, $MTXPG_7$ is MTXPG having seven glutamates, and $MTXPG_{2-7}$ is a mixture containing $MTXPG_2$, $MTXPG_3$, $MTXPG_4$, $MTXPG_5$, $MTXPG_6$ and $MTXPG_7$ with the ratio of the individual polyglutamated forms in the mixture not defined. It is understood that, consistent with this nomenclature, $MTXPG_1$ is synonymous with MTX.

An extract from cells that have taken up MTX will typically contain a mixture of methotrexate polyglutamated species that differ in the number of attached glutamate moieties. Such mixtures of MTXPGs can be efficiently converted to MTX by a method of the invention as set forth below and demonstrated in Examples II and III. A method of the invention can also be used to efficiently convert MTXPGs that are homogeneous with respect to the number of attached glutamate moieties as demonstrated by the efficient conversion of $MTXPG_2$ to MTX in Example II. In particular embodiments, the methods of the invention are used to efficiently convert an $MTXPG_n$ to MTX, where n is any integer greater than 1.

In a method of the invention, MTXPGs can be converted to MTX by gamma glutamyl hydrolase. As used herein, the term "gamma glutamyl hydrolase" is synonymous with "GGH" and means a molecule that catalyzes cleavage of a gamma glutamyl bond to remove a glutamate moiety from a polyglutamated substrate. In one embodiment of the invention, a GGH catalyzes cleavage of a gamma glutamyl bond to remove a glutamate moiety from a polyglutamated substrate and lacks activity in cleaving the glutamate moiety from a monoglutamated substrate. GGHs useful in the invention including, but are not limited to, enzymes such as EC 3.4.19.9, or a functional equivalent thereof including, for example, gamma-glu-X carboxypeptidase, folate conjugase, pteroyl-poly-alpha-glutamate hydrolase, carboxypeptidase G and lysosomal gamma-glutamyl carboxypeptidase. Examples of substrates of a gamma glutamyl hydrolase are MTXPGs and other polyglutamated antifolates. It is understood that a GGH can catalyze removal of any number of glutamate residues that are linked to the gamma carboxyl of a monoglutamated moiety of a polyglutamated substrate, and under certain conditions can yield a monoglutamated product. As an example, $MTXPG_n$ includes n-1 glutamates that can be catalytically removed by GGH; $MTXPG_2$ includes a single glutamate that can be catalytically removed by GGH; and $MTXPG_7$ includes 6 glutamates that can be catalytically removed by GGH. As discussed further below, it is understood that the actual number of glutamates hydrolyzed, if any, depends on the conditions and length of time the enzyme is in contact with the polyglutamated substrate.

In one embodiment of the invention, a GGH is in contact with a cellular extract under conditions suitable for cleavage of a gamma glutamyl bond such that all but one glutamate moiety are cleaved from a polyglutamated substrate. As an example, carboxypeptidase G is a GGH that under particular conditions can convert MTXPG to MTX and, additionally, can remove the glutamate moiety from MTX to yield 4-amino-4-deoxy-$N^{10}$-methylpteroic acid (DAMPA). Carboxypeptidase G can be used to convert MTXPG to MTX in a method of the invention under conditions that reduce or prevent the latter activity, such as in the presence of an inhibitor, thereby removing all but one glutamate moiety from MTXPGs and converting the MTXPGs to MTX.

Native gamma-glutamyl hydrolase is a glycoprotein typically having a molecular mass of 80 to 120 kDa (Yao et al., *Proc. Natl. Acad. Sci. USA* 93:10134-10138 (1996)). The protein portions of human and rat GGH are about 35 kDa with multiple potential asparagine-linked glycosylation sites, rat GGH having seven and human GGH having four based on sequence homology (Yao et al., supra, 1996). Depending upon the tissue, GGH is found in lysosomal compartments or secreted (Yao et al., *J. Biol. Chem.* 271:8525-8528 (1996)). GGH typically has an acidic pH optimum and is often sulfhydryl- and $Zn^{2+}$-dependent (Yao et al., *J. Biol. Chem.* 271: 8525-8528 (1996)).

A variety of GGHs are useful in the invention, including those with naturally occurring and non-naturally occurring sequences, glycosylated and non-glycosylated forms, species homologs, or in crude, partially purified or purified forms. GGHs useful in the invention include, without limitation, biochemically purified native proteins as well as recombinant proteins and fragments or isoforms thereof that retain gamma glutamyl hydrolase activity. A variety of GGHs can be useful in the invention including, but not limited to, mammalian, primate, human, non-human primate, bovine, porcine, rat, and murine GGHs. Furthermore, GGHs with improved or diminished enzymatic activity, stability or other function as compared to naturally occurring (wild type) GGH can be useful in the invention, as can point mutants, deletion or insertion mutants and fusion proteins including GGH or an active fragment thereof. In particular embodiments, the invention is practiced with a source containing a GGH with at least 40% amino acid identity to the human GGH provided in Genbank accession NM_003878, or with at least 50%, 60%, 70%, 80%, 90% or more amino acid identity as compared to the human GGH provided in Genbank accession NM_003878.

A GGH useful in the invention can be provided, without limitation, as plasma or a fraction thereof; or as an extract from a cell expressing GGH or a fraction thereof; or in any purified or partially purified form. Under optimal conditions, a GGH can have, for example, an activity of at least 30% conversion of $MTXPG_2$ to MTX per hour, for example, at least 25% conversion of $MTXPG_2$ to MTX per hour, or at least 10% conversion of $MTXPG_2$ to MTX per hour. A GGH can be a GGH of any species origin, for example, a human GGH having NCBI Accession NM_003878 (see, also, Rhee et al., *Mol. Pharmacol.* 53: 1040-1046 (1998), and Yao et al., *Proc. Natl. Acad. Sci. USA* 93:10134-10138 (1996)); the rat GGH having NCBI Accession NM_012960 (see, also, Yao et al., *J. Biol. Chem.* 271: 8525-8528 (1996)); or the mouse GGH having NCBI Accession NM_010281 (see, also, Esaki et al., *Gene* 234:93-100 (1999)).

Plasma containing GGH can be used to efficiently convert MTXPGs to MTX as demonstrated in Examples II and III. As used herein, the term "plasma" means the acellular fluid portion of blood. Plasma useful in a method of the invention can be obtained from any of a variety of animals. As non-limiting examples, plasma useful in the invention can be human plasma, primate plasma, non-human primate plasma, rat plasma, mouse plasma or plasma from any other mammal. Plasma can be used in the invention as fresh plasma or, alternatively, following storage under conditions that maintain GGH activity. Plasma can be obtained using methods well known in the art such as centrifugation of blood at low speed and isolation of the supernatant fraction. Plasma can also be obtained from a commercial source, such as Sigma (St Louis, USA), which provides lyophilized plasma (Cat. No. P9523). Exemplary conditions that can be used to store plasma useful in the invention include, without limitation, lyophilization, refrigeration, freezing or a combination thereof.

A cell expressing GGH also can be a source of GGH useful in a method of the invention. Such a cell can be any cell that expresses endogenous or recombinant GGH or both. Many cancer cells, including, for example, human breast cancer cells, hepatoma cell lines and leukemia cell lines are known to express high levels of GGH and can therefore serve as sources of GGH for use in the invention. See, for example, Rhee et al., *Cell Pharmacol.* 2:289-292 (1995), and Pizzorno et al., *Cancer Res.* 55:566-573 (1995).

It further is understood that GGH can be obtained from a recombinant cell that expresses exogenous GGH. Nucleic acid molecules encoding GGH are known in the art, as set forth above, or can be obtained by routine cloning methods including, for example, isolation of a GGH-encoding nucleic acid molecule from a cDNA library or genomic library with a natural or artificially designed gene-specific nucleic acid probe, or PCR amplification using a sequence specific primer. The GGH-encoding nucleic acid molecule can be cloned into an expression vector and used to transform cells for recombinant expression of GGH by routine methods, as described for human and rat GHH, for example, in Rhee et al., supra, 1998, and Yao et al., supra, 1996. Those skilled in the art will be able to obtain recombinant cells expressing any of a variety of GGHs using these and other routine cloning methods that are well known in the art as described, for example, in Sambrook et al., *Molecular Cloning: A Laboratory Manual,* 3rd ed., Cold Spring Harbor Press, Plainview, N.Y. (2001); and Ausubel et al. (*Current Protocols in Molecular Biology* (Supplement 47), John Wiley & Sons, New York (1999).

Purified or partially purified GGH also can be useful in a method of the invention. As non-limiting examples, GGH can be obtained from a native source such as plasma or a tumor cell or a recombinant source such as a bacterial, yeast or insect cell. GGH can be purified or partially purified using known methods as described, for example, in Scopes, *Protein Purification: Principles and Practice,* $3^{rd}$ Ed., Springer-Verlag, New York (1994) and Coligan et al., *Current Protocols in Protein Science,* John Wiley and Sons, Baltimore, Md. (2000). Isolation of GGH by these and other methods can be monitored using an antibody to GGH or an assay for GGH activity as described, for example, in Yao et al., supra, 1996, or Rhee et al., supra, 1998. As a non-limiting illustration, an *E. coli* cell lysate containing recombinant human gamma glutamyl hydrolase can obtained by sonicating *E. coli* cells that express the recombinant enzyme as described, for example, in Yao et al., supra, 1996. As a further illustration, recombinant human gamma glutamyl hydrolase can be expressed in intracellular or secreted form using recombinant insect cells and purified with cation exchange chromatography or immunoaffinity chromatography as described, for example, in Rhee et al., supra, 1998.

The methods of the invention involve contacting a cellular extract with gamma glutamyl hydrolase under conditions suitable for efficient conversion of MTXPGs to MTX. As used herein, the term "efficient conversion" means the production at least a 60% molar equivalent of MTX product compared to MTXPG substrate. Thus, the phrase "under conditions suitable for efficient conversion of MTXPGs to MTX"

means an environment in which at least a 60% molar equivalent of MTX is produced from MTXPGs. In particular embodiments, the methods of the invention for efficiently converting MTXPGs to MTX produce at least 65%, 70%, 75%, 80%, 85%, 90%, 95%, 98% or 99% molar equivalent of MTX product compared to MTXPG substrate. In addition embodiments, the methods of the invention produce at least 60%, 65%, 70%, 75%, 80%, 85%, 90%, 95%, 98% or 99% molar equivalent of MTX product from $MTXPG_2$ substrate. Efficient conversion of $MTXPG_2$ to MTX can occur within a time period of, for example, 2 hours, 4 hours, 6 hours, 8 hours, 10 hours, 12 hours or longer. Thus, at least 65%, 70%, 75%, 80%, 85%, 90%, 95%, 98% or 99% molar equivalent of MTX product compared to MTXPG substrate can be produced, for example, within 2 hours, 4 hours, 6 hours, 8 hours, 10 hours, 12 hours or longer.

In one embodiment, a method of the invention is practiced by converting MTXPGs to MTX under conditions that include a pH of at least 4. The methods of the invention can be practiced, for example, under conditions that include a pH in the range of about 6 to 7. It is understood that the desired pH can be maintained using a buffer. Those skilled in the art can determine an appropriate buffer to maintain a particular pH based on the pKa of the sample being used and known pKa values of buffers as described, for example, in Segel, *Biochemical Calculations,* 2nd Ed., John Wiley and Sons, New York (1976). As illustrated in Example II, because plasma and RBCs are strongly buffered at physiological pH, addition of 100 mM phosphate buffer pH 4.5 to a mixture of plasma and RBC extract at a volume/volume ratio of 2 parts buffer:1 part RBC extract:2 parts plasma yields a final pH of about 6.5. Those skilled in the art will recognize that buffers having a similar pKa can be substituted for each other in order to maintain a desired pH in a method of the invention. The concentration of phosphate in the conditions of the invention can be, for example, below about 400 mM such as below 350 mM or below 300 mM.

By using an appropriate buffer, a method of the invention can be practiced under conditions that include, for example, a pH of about 3.5, 4.0, 4.5, 5.0, 5.5, 6.0, 6.5, 7.0, 7.5, 8.0 or 8.5. In particular embodiments, a method of the invention is practiced under conditions that include a pH of at least 3.5, at least 4.0, at least 4.5, at least 5.0, at least 5.5, at least 6.0, at least 6.5 or at least 7.0. In other embodiments, a method of the invention is practiced with a pH in the range of 4.0 to 8.0, 4.5 to 8.0, 5.0 to 8.0, 5.5 to 8.0, 6.0 to 8.0, 6.5 to 8.0, 7.0 to 8.0, 4.0 to 7.5, 4.0 to 7.0, 4.0 to 6.5, 4.0 to 6.0, 5.0 to 7.5, 5.0 to 7.0, 5.0 to 6.5, 5.0 to 6.0, 6.0 to 7.0, or 6.5 to 7.0.

Conditions suitable for efficient conversion of MTXPGs to MTX can include, for example, a reducing agent as demonstrated in Example II, where 2-mercaptoethanol was included. The concentration of 2-mercaptoethanol in a method of the invention can be, for example, about 50 mM or more. Other reducing agents can be useful in the invention including, without limitation, dithiothreitol, dithionite, cysteamine or glutathione. It is understood that the concentration of the reducing agent can vary from those exemplified herein, so long as the conditions lead to efficient conversion of MTX-PGs to MTX.

Efficient conversion of at least 60% $MTXPG_{2-7}$ to MTX typically occurs within about 3 hours or less using plasma as a source of GGH. As an example, FIG. 4A shows that GGH provided in a plasma fraction converted greater than 60% $MTXPG_2$ to MTX in about 3 hours and greater than 90% $MTXPG_2$ to MTX in about 5 hours. As a further example, FIG. 4B shows that GGH provided in a plasma fraction converted greater than 60% $MTXPG_{2-7}$ to MTX in about 2 hours and greater than 90% $MTXPG_{2-7}$ to MTX in about 5 hours. Those skilled in the art will understand that the time for the conversion reaction can be altered from the times used for plasma GGH as exemplified herein depending, for example, on the use of a more concentrated or purified fraction of GGH, recombinant GGH or another molecule having GGH activity. As non-limiting examples, a method of the invention can be practiced by contacting a cellular extract containing MTX-PGs with plasma or another source of with gamma glutamyl hydrolase for a time that is within the range of 2 to 15 hours, 2 to 10 hours, 2 to 8 hours, 2 to 5 hours, 3 to 15 hours, 3 to 10 hours, 3 to 8 hours, 3 to 5 hours, 5 to 15 hours, 5 to 10 hours, 5 to 8 hours, 6 to 24 hours, 9 to 24 hours, 6 to 15 hours or 9 to 15 hours.

Plasma used as a source of GGH in a method of the invention can be provided, for example, in a volume excess of about 2 fold or more compared to the volume of a RBC extract, provided at a concentration of about $0.5 \times 10^9$ red blood cells per 100 microliters. As exemplified in Example II, MTXPGs were efficiently converted to MTX in a RBC extract using a 2 fold excess of plasma that had been reconstituted from lyophilized form according to the manufacturer's instructions. Although more concentrated conditions can be used in a method of the invention, precipitation of some of the MTX-PGs by hemoglobin in the mixture can reduce the amount that is converted to MTX. Higher volume excess of plasma to RBC extract can also be used such as 2.5 fold, 3 fold, 3.5 fold, 4 fold or higher volume excess of plasma compared to RBC extract, so long as MTXPGs are efficiently converted to MTX. Those skilled in the art will recognize that dilution of RBC's in a method of the invention can be achieved in other ways including, without limitation, increasing the volume of buffer present or decreasing the number of RBC's present. For example, when purified GGH or GGH from recombinant cells or enriched plasma fractions is used in place of plasma in a method of the invention, the concentration of the RBC's can be diluted, if desired, using buffer.

In a method of the invention MTXPGs are efficiently converted to MTX in a cellular extract. As used herein, the term "cellular extract" means a mixture containing a heterogenous plurality of cellular components. A cellular extract useful in the invention can contain, for example, a heterogeneous plurality of soluble cellular compounds, proteins or metabolites. Heterogeneity of a cellular extract can be characterized by various criteria. According to one criteria, a cellular extract useful in the invention can be heterogeneous with respect to the variety of cellular components present in the extract. In this regard, a cellular extract can contain, for example, at least 100, 1000, $1 \times 10^4$ or $1 \times 10^5$ or more different cellular components, for example, at least 100, 1000, $1 \times 10^4$ or $1 \times 10^5$ or more different proteins. Heterogeneity can also be expressed as the percent of the total number of different components of the cell from which the extract is derived. For example, a cellular extract can contain cellular components representing at least 5%, 10%, 15%, 20%, 25%, 50% or 75% of the variety of components present in the cell from which the extract was derived. Heterogeneity can also be determined based on the percentage of any one cellular component in a cellular extract compared to the total amount of other components in the cellular extract. A cellular extract useful in the invention can have, for example, a cellular component that represents at most about 90%, 80%, 70%, 60%, 50%, 25%, or 10% of the total amount of other cellular components in the mixture. A cellular extract used in a method of the invention can contain mixtures of components such as proteins, components that are larger than 100 Da or components that absorb radiation between about 303 nm and 313 nm or at about 370 nm.

A cellular extract that is useful in a method of the invention can be any cell extract that contains one or more MTXPGs. Additional exogenous MTXPGs can be added to a cellular extract as set forth in Example II. The addition of one or more exogenous MTXPGs into a cellular extract can be useful for determining a standard curve for quantitating MTX or for otherwise testing or optimizing MTX detection conditions. A cellular extract containing MTXPGs can be obtained by adding MTX to a cellular extract and allowing polyglutamation to occur in vitro. Thus, a method of the invention can be used to monitor or determine polyglutamation activity of a cell or a component thereof, such as folylpoly-gamma-glutamate synthetase. A cellular extract can also be prepared from a cell isolated from an individual that has been administered methotrexate by any route. Efficient conversion of MTXPGs to MTX in a cellular extract obtained from an individual undergoing low-dose MTX therapy is disclosed in Example III. The method of the invention for efficiently converting MTXPGs to MTX in a cellular extract from an individual treated with methotrexate can be useful for optimizing therapeutic efficacy or reducing toxicity associated with MTX therapy in the individual, as set forth in greater detail below.

The methods of the invention are well suited to efficiently converting MTXPGs to MTX in a red blood cellular extract as demonstrated in Examples II and III. The conditions exemplified herein can also be readily applied to other types of cellular extracts in order to efficiently convert MTXPGs to MTX. The cellular extract can be from a cell that is a target for MTX therapy or otherwise is a cell indicative of efficacy or toxicity of MTX therapy. Non-limiting examples of cellular extracts that are useful in the invention include extracts prepared from tissue biopsies, erythrocyte extracts, neutrophil extracts and leukocyte extracts. Additional cellular extracts useful in the invention include neoplastic or cancer cell extracts such as those obtained from any of the specific cancers set forth below. Cellular extracts useful in a method of the invention further include, without limitation, mammalian cellular extracts, primate cellular extracts, human cellular extracts, non-human primate cellular extracts, rat cellular extracts, mouse cellular extracts, cat cellular extracts, dog cellular extracts, bird cellular extracts and horse cellular extracts.

A cellular extract useful in the invention can be obtained from any individual treated with methotrexate therapy, including low-dose and high-dose therapy. In one embodiment, a cellular extract useful in a method of the invention is from an individual having an autoimmune disease. As used herein, the term "autoimmune disease" means a disease resulting from an immune response against a self tissue or tissue component and can include a self antibody response or cell-mediated response. The term autoimmune disease, as used herein, encompasses organ-specific autoimmune diseases, in which an autoimmune response is directed against a single tissue, such as Crohn's disease and ulcerative colitis, Type I diabetes mellitus, myasthenia gravis, vitiligo, Graves' disease, Hashimoto's disease, Addison's disease and autoimmune gastritis; and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include pernicious anemia, autoimmune gastritis, primary biliary cirrhosis, autoimmune thrombocytopenia, Sjögren's syndrome, multiple sclerosis and psoriasis. One skilled in the art will know that a number of the autoimmune diseases set forth above have been treated with MTX therapy or can be treated with MTX therapy. One skilled in the art recognizes that the methods of the invention can be used with a cellular extract obtained from an individual having any of the above or another autoimmune disease.

In another embodiment a cellular extract useful in a method of the invention is obtained from an individual having arthritis. As used herein, the term "arthritis" means an inflammatory condition that affects joints. Arthritis can be infective, autoimmune or traumatic in origin; the term arthritis includes, but is not limited to, acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, juvenile rheumatoid arthritis, venereal arthritis, and viral arthritis.

In a further embodiment a cellular extract useful in a method of the invention is obtained from an individual having rheumatoid arthritis. Rheumatoid arthritis is a chronic systemic disease primarily of the joints, usually polyarticular, marked by inflammatory changes in the synovial membranes and articular structures and by muscle atrophy and rarefaction of the bones. Methotrexate is widely used in the treatment of rheumatoid arthritis, and one skilled in the art recognizes that the methods of the invention can be practiced with a cellular extract from an individual having rheumatoid arthritis or another form of arthritis.

In another embodiment, a method of the invention is practiced with a cellular extract from an individual having cancer. As used herein, the term "cancer" is intended to mean any member of a class of diseases characterized by the uncontrolled growth of aberrant cells. The term includes all known cancers and neoplastic conditions, whether characterized as malignant, benign, soft tissue or solid tumor and cancers of all stages and grades including pre- and post-metastatic cancers. The term cancer encompasses, without limitation, leukemias such as acute lymphocytic leukemia and acute myelocytic leukemia; lymphomas; choriocarcinomas; head and neck cancers; and osteogenic sarcomas, each of which are widely treated with methotrexate. The term cancer further includes, but is not limited to, digestive and gastrointestinal cancers such as anal cancer, bile duct cancer, gastrointestinal carcinoid tumors and colon cancer; esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; cancer of the central nervous system; and skin cancer. In a particular embodiment, a method of the invention is practiced with a cellular extract obtained from an individual having leukemia.

Rheumatoid arthritis and a variety of other autoimmune disorders such as psoriasis, systemic lupus erythematosus, and graft-versus-host disease are typically treated with low-dose MTX therapy, which is also used in some cancer treatment regimens. In one embodiment, a method of the invention is practiced with a cellular extract from an individual undergoing low-dose MTX therapy. As used herein, the term "low-dose MTX therapy" means administration of MTX to an individual at a dose that is less than 40 mg/m$^2$ of body surface per week. Typically, low-dose MTX therapy is administered at a dose in the range of 2.5 to 40 mg/m$^2$ of body surface per week depending upon the condition being treated. Low-dose MTX therapy is typically administered orally because relatively low doses of MTX are absorbed by the gastrointestinal tract.

The methods of the invention can also be used with a cellular extract from an individual undergoing high-dose MTX therapy, for example, for treatment of cancer. As used herein, the term "high-dose MTX therapy" means administration of MTX to an individual at a dose that is at least 40 mg/m$^2$ of body surface per day, for example, at least 100, 500, 1000, 1500, 3000 mg/m$^2$ or 5000 mg/m$^2$ of body surface per day. One skilled in the art understands that high-dose MTX therapy can be administered at doses up to 5 g/m$^2$ of body surface per day or higher depending upon the condition or disease being treated. One skilled in the art recognizes that the doses of MTX typically used in high-dose MTX therapy can be administered, for example, intravenously or orally and that such high-dose MTX therapy generally requires a period of recovery, which can include leucovorin rescue or other forms of folate replacement.

It will be understood that the dosage ranges of MTX set forth above in the definitions of high- and low-dose MTX therapy are generalized with respect to treatment of a variety of diseases and that the range of MTX dose that is administered for one disease can differ from the range administered for another. Accordingly, a dose of 40 mg/m$^2$ of body surface per day, although generally considered high-dose MTX therapy, may be considered by those skilled in the art of cancer therapy as a relatively low dose for treating cancer. Similarly, a dose of 30 mg/m$^2$ of body surface per day, although generally considered as low-dose MTX therapy, may be considered by those skilled in the art of rheumatology as a relatively high-dose for treating rheumatoid arthritis.

Cellular extracts useful in the invention can be prepared from a cell or tissue using methods well known in the art. Those skilled in the art will know or be able to determine an appropriate method for obtaining source cells based on their location and characteristics. As an example, red blood cells and other blood cells can be obtained by harvesting through intravenous routes. Cells can also be removed from tissues, such as cancer tissues, using known biopsy methods including, for example, those utilizing an open surgical incision, biopsy needle or endoscope. Cells will be lysed by any of a variety of means depending, in part, on the properties of the cell. As non-limiting examples, cells can be lysed by mechanical disruption with glass beads, a Dounce homogenizer, french press, or sonication; enzymatic disruption with lysozyme or other enzyme that degrades the cell wall; osmotic disruption or a combination of these methods.

A cellular extract useful in a method of the invention can be a fractionated extract, which can be enriched in MTX or MTXPGs as compared to the total extract. As an example, an extract can be fractionated by centrifugation to remove insoluble material such as membranes and large cellular structures. Fractionation to separate MTX, MTXPGs, or analogs thereof, from other cellular components can include, without limitation, centrifugation, protein precipitation, liquid-liquid extraction, solid-phase extraction, or chromatography such as reverse phase chromatography, ion pairing chromatography or ion exchange chromatography, as described, for example, in Rubino, *J. Chromatog.* 764:217-254 (2001). Additional methods that can be used to obtain and fractionate cellular extracts are well known in the art, as described, for example, in Scopes, supra, 1994, and Coligan et al., supra, 2000.

The methods described above for efficiently converting MTXPGs to MTX also can be used to efficiently deglutamate other glutamated and polyglutamated substrates, including polyglutamated antifolates. A number of antifolates useful in treating diseases and conditions characterized by aberrant cell proliferation can be polyglutamated in cells. Such antifolates are advantageous for therapeutic use because intracellular derivatization of an antifolate with polyglutamate prevents the derivatized antifolate from being extruded from the cell, in contrast to monoglutamated antifolates, which are generally extruded. Thus, a polyglutamated antifolate is maintained in a cell for long periods of time and, consequently, has prolonged cytotoxic activity without requiring high levels of administration.

Thus, the invention provides a method for efficiently deglutamating a polyglutamated substrate in a cellular extract by contacting the cellular extract with gamma glutamyl hydrolase under conditions suitable for efficiently converting the polyglutamated substrate to a monoglutamated substrate or an unglutamated substrate. The invention also provides a method for efficiently deglutamating a polyglutamated antifolate in a cellular extract by contacting the cellular extract with gamma glutamyl hydrolase under conditions suitable for efficient conversion of the polyglutamated antifolate to an antifolate. Such conditions allow gamma glutamyl hydrolase to remove glutamates from polyglutamated antifolates by cleavage of one or more iso-peptide bonds.

As used herein, the term "antifolate" means a molecule having structural similarity to folate and activity as a folate antagonist against one or more folate-dependent enzymes. Polyglutamylatable antifolates are antifolates that can be polyglutamated in a cell by an enzyme such as folylpoly-gamma-glutamate synthetase. Examples of polyglutamylatable antifolates include, without limitation, aminopterin, raltitrexed, lometrexol, multitargeted antifolate (MTA), AQA, MTX and analogs thereof. Aminopterin, for example, possesses a hydrogen instead of a methyl group at position N-10 compared to the structure of methotrexate. Raltitrexed is a selective inhibitor of thymidylate synthase as described, for example, in Kamen, *Semin. Oncol.* S18:30-39 (1997). Lometrexol selectively inhibits glycinamide ribonucleotide formyltransferase, the first enzyme involved in the pathway of de novo purine synthesis as described, for example, in Calvert, supra, 1999. MTA is an inhibitor of multiple folate-dependent enzymes, such as dihydrofolate reductase, thymidylate synthase, and glycinamide ribonucleotide formyltransferase (see, for example, Calvert, supra, 1999).

One type of antifolate useful in the invention is a methotrexate analog. As used herein, the term "methotrexate analog" means a molecule having structural and functional similarity to methotrexate. Methotrexate analogs are functionally characterized, in part, by their inhibitory activity against dihydrofolate reductase. A methotrexate analog useful in the invention acts as a substrate for polyglutamation in a cell by an enzyme such as folylpoly-gamma-glutamate synthetase. MTX analogs include, but are not limited to, 4-amino derivatives with halogen substitution on the para-aminobenzoic moiety, such as dichloromethotrexate (see, for example, Frei et al., *Clin. Pharmacol. Therap.* 6:160-71 (1965)); 7-methyl substituted MTX (see, for example, Rosowsky and Chen, *J. Med. Chem.* 17:1308-11 (1974)); 3',5'-difluoro MTX, (see, for example, Tomcuf, *J. Organic Chem,* 26:3351 (1961)); 2' and 3' monofluorinated derivatives of aminopterin (see, for example, Henkin and Washtien, *J. Med. Chem.* 26:1193-1196 (1983)); and 7,8-dihydro-8-methyl-MTX (see, for example, Chaykovsky, *J. Org. Chem.* 40:145-146 (1975)). The skilled person understands that the methods of the invention can be used to optimize or monitor efficacy or toxicity associated with methotrexate analogs or other antifolates in the same manner as disclosed herein for monitoring methotrexate therapy.

The invention further provides a method for determining a level of methotrexate polyglutamates in a cellular extract. The method includes the steps of: (a) converting the MTXPGs to methotrexate in a cellular extract under conditions suitable for efficient conversion of MTXPGs to MTX, and (b) determining a level of the MTX, where the level of MTX can be correlated with the level of MTXPGs in the cellular extract. Step (a) of the method can further include, for example, contacting the cellular extract with gamma glutamyl hydrolase under conditions suitable for efficient conversion of MTXPGs to MTX, for example, any of the conditions set forth above. The method is useful for monitoring the efficacy or toxicity of MTX therapy, as set forth in further detail below.

As discussed above, the invention provides conditions suitable for efficient conversion of MTXPGs to MTX. Thus, the level of MTX in a "converted" cellular extract can be correlated with the level of MTXPGs in the cellular extract after correction for any baseline level of methotrexate. The term "level," when used in reference to a particular molecule in a sample, means an amount or concentration of the particular molecule in the sample. As an example, a level of MTX within a cellular extract is the amount or concentration of MTX in the cellular extract; a level of MTXPGs in a cellular extract is the amount or concentration of MTXPGs in the cellular extract. In view of the above, it is understood that a level can be an absolute level such as a molar concentration or weight or a relative level such as a percent or fraction compared to one or more other molecules in a sample. Specifically excluded from the definition of "level," as used herein, are estimates or measurements based on enzymatic activity, such as inhibition of DHFR or other enzyme activity.

Subsequent to efficient conversion of methotrexate polyglutamates to methotrexate, the methods of the invention can include a step of determining the level of methotrexate. Quantitative and accurate detection of MTX at low levels in cellular extracts can be achieved using the methods set forth below.

The invention also provides a method for determining a level of methotrexate in a cellular extract by (a) irradiating the cellular extract, thereby producing a fluorescent MTX photolytic product; and (b) determining a level of the fluorescent MTX photolytic product, wherein the level of the fluorescent MTX photolytic product can be correlated with the level of MTX. By indirectly determining the intracellular level of methotrexate polyglutamates, a method of the invention can be useful for monitoring the efficacy or toxicity of MTX therapy.

In a method of the invention, MTX can be irradiated to produce a photolytic product. As used herein, the term "photolytic product" means a molecule that is produced by cleavage of bonds in a substrate that is electronically excited by radiation. The process of producing a photolytic product is referred to as photolysis. Photolysis of MTX to produce a "MTX photolytic product" can be performed, for example, with UV light, which is a term understood in the art to include any wavelength in the range of about 200 to 400 nm. It further is understood that any light source which produces UV light can be useful in a method of the invention including, for example, a lamp such as an arc lamp or quartz halogen lamp, or a laser. As demonstrated in Example I, a fluorescent MTX photolytic product was produced by irradiating MTX with a low pressure mercury UV lamp which emits radiation in the range of 225 to 275 nm and has a peak output at 254 nm. It is understood that MTX can be selectively irradiated with a particular wavelength in the UV range by using an appropriate light source, optical filter or combination of these components in accordance with their known optical characteristics.

A sample, such as a cellular extract, that contains MTX, can be irradiated according to a method of the invention for the appropriate period of time to yield a fluorescent MTX photolytic product, where the level of the fluorescent MTX photolytic product can be correlated with the level of MTX in the sample. In particular embodiments, a method of the invention is practiced by irradiating a cellular extract containing MTX for 0.5 to 60 seconds. Shorter periods of irradiation within this range can also be useful in a method of the invention including, for example, irradiation for 0.5 to 15 seconds. In further embodiments, the cellular extract is irradiated for 0.1 to 100 seconds, 0.2 to 60 seconds, 0.5 to 60 seconds, 0.5 to 45 seconds, 0.5 to 30 seconds, 0.5 to 20 seconds, 0.5 to 15 seconds, 0.5 to 10 seconds, 1 to 20 seconds, 1 to 10 seconds, 2 to 20 seconds or 2 to 10 seconds. In additional embodiments, the cellular extract is irradiated for 0.5 to 6, 0.5 to 5, 0.5 to 4, 1 to 6, 1 to 5, 1 to 4, or 2 to 4 seconds.

As demonstrated in Example I, irradiation for 3 seconds yielded primarily fluorescent MTX photolytic product A. As further demonstrated in Example I, irradiation for 24 seconds yielded primarily fluorescent MTX photolytic product B. In view of the above, it is understood that the time of irradiation can be varied to produce the desired fluorescent MTX photolytic product having characteristic properties as desired for a particular application. One skilled in the art further understands that the methods of the invention can be practiced by detecting a single fluorescent MTX photolytic product such as MTX photolytic product A or MTX photolytic product B. The MTX photolytic products A and B have different properties including, for example, characteristic fluorescence excitation and emission peak maxima, and characteristic fluorescence intensity levels depending upon the pH and amount of acetonitrile present during detection (see Example I).

Photolysis of MTX can be carried out in the presence of hydrogen peroxide ($H_2O_2$) or another peroxide. As a non-limiting example, when hydrogen peroxide is added, the final concentration can be 0.03% or higher. In particular embodiments, the final concentration of hydrogen peroxide is in the range of 0.05% to 1%, 0.2% to 1% or 0.3% to 0.6%.

A level of MTX in a cellular extract can be determined based on the level of a fluorescent MTX photolytic product. The term level, when used in reference to a fluorescent MTX photolytic product, means an amount or concentration of the fluorescent MTX photolytic product. The amount or concentration of a fluorescent MTX photolytic product can be determined, for example, based on the intensity of fluorescence from the photolytic product.

As used herein, the term "fluorescence" means an emission of photons in the ultraviolet (UV), visible (VIS) or infrared (IR) region of the spectrum in response to electronic excitation by radiation. The term "fluorescent," when used in reference to a MTX photolytic product, means a photolytic product that emits photons in the UV, VIS or IR region of the spectrum in response to electronic excitation by radiation. Thus, a fluorescent MTX photolytic product is a photolytic product derived from methotrexate that emits photons in the UV, VIS or IR region of the spectrum in response to electronic excitation by radiation. A fluorescent MTX photolytic product can be characterized, for example, as emitting photons at a quantum yield of at least 0.01 when excited by radiation in solution. In particular embodiments, a fluorescent MTX photolytic product is characterized by a quantum yield of fluorescence that is at least 0.1, 0.2, 0.3, 0.4, 0.5, 0.6, 0.7, 0.8, 0.9 or higher when excited by radiation in solution.

A fluorescent molecule, such as a fluorescent MTX photolytic product, also can be characterized with respect to maximum emission wavelength or maximum excitation wavelength. In particular embodiments, a method of the invention involves determining the level of a fluorescent MTX photolytic product having a maximum excitation wavelength in the IR, red, orange, yellow, green, blue, violet or UV region of the spectrum. In additional embodiments, a method of the invention is practiced by determining the level of a fluorescent MTX photolytic product having a maximum emission wavelength in the IR, red, orange, yellow, green, blue, violet or UV region of the spectrum.

Figure 2:
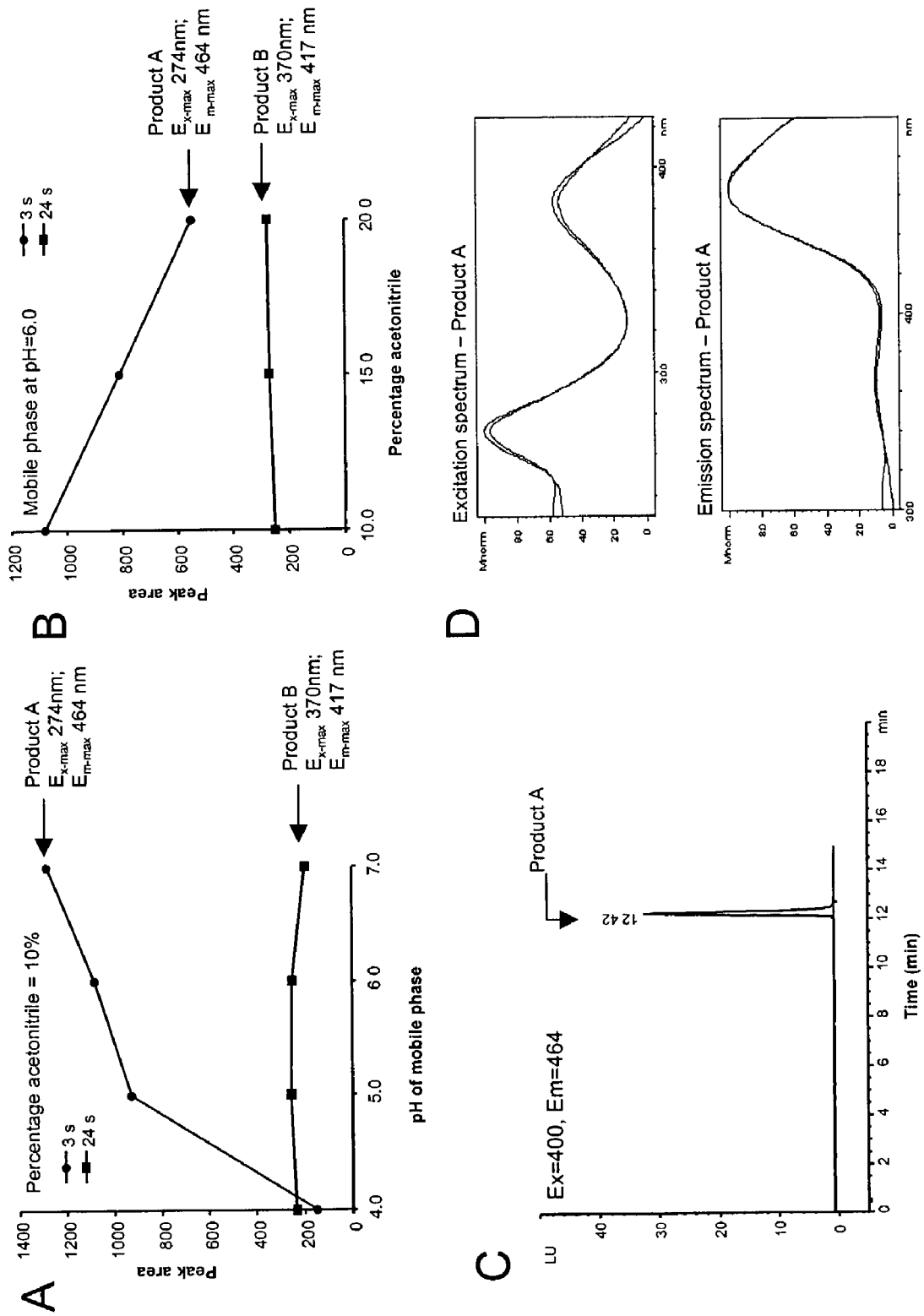
FIG. 2 shows the effect of mobile phase composition on formation of fluorescent MTX photolytic products. (A) A plot of peak area detected at different pH values for MTX photolytic product A or product B; (B) A plot of peak area detected at different acetonitrile concentrations for MTX photolytic product A or product B; (C) A chromatogram of the photolytic products of MTX; and (D) Fluorescence excitation and emission spectra for photolytic product A of the compound eluting at 12.42 min from two separate chromatography runs.

Fluorescence can be detected in a method of the invention using any of a variety of excitation sources and emission detectors. Excitation of a fluorescent MTX photolytic product can be achieved with an excitation source such as a lamp or laser including, without limitation, any of those described above in regard to photolysis. Excitation at a particular wavelength or in a particular wavelength range can be achieved in a method of the invention using, for example, a laser that is tuned to the desired wavelength or a lamp having an output that includes the wavelength range. An appropriate optical filter can be placed between the excitation source and fluorescent MTX photolytic product to further limit the range of wavelengths contacting the fluorescent MTX photolytic product if desired. As shown in FIG. 2D and set forth in Example I, fluorescent MTX photolytic product A has two excitation peaks in the range of 240 nm to 420 nm, including the peak from about 240 nm to 300 nm and the peak from about 360 nm to 410 nm. In particular embodiments of the invention, a fluorescent MTX photolytic product can be detected by excitation at a wavelength in the range of about 240 nm to 420 nm, about 240 nm to 300 nm or about 360 nm to 410 nm. If desired, the methods of the invention can include excitation at or near the peak of 275 nm or in a range near this peak including, for example, excitation at a wavelength in the range of 250 nm to 290 nm or 260 nm to 280 nm. An excitation at or near the peak of 385 nm or in a range near this peak can also be used including, for example, excitation at a wavelength in the range of 250 nm to 290 nm or 260 nm to 280 nm.

Emission can be detected from a fluorescent MTX photolytic product using a detector such as, without limitation, a photomultiplier tube, diode, diode array or charge coupled device camera. A detector that detects light at a particular wavelength or in a particular wavelength range can be used in a method of the invention. If desired, an optical filter can be placed between the fluorescent MTX photolytic product and the detector to limit the range of wavelengths detected. As shown in FIG. 2D and set forth in Example I, fluorescent MTX photolytic product A emits from about 320 nm to 550 nm and has a primary peak from about 440 nm to 520 nm. In particular embodiments of the invention, emission from a fluorescent MTX photolytic product can be detected at a wavelength in the range of about 320 nm to 550 or about 440 nm to 520 nm. If desired, the methods of the invention can include detection of emission at or near the peak of 464 nm or in a range near this peak including, for example, emission at a wavelength in the range of 450 nm to 510 nm or 460 nm to 490 nm.

A level of MTX also can be determined using, for example, chromatography or mass spectrometric analysis. MTX can be chromatographically separated from other cellular components using, for example, reverse phase chromatography as set forth in Examples I through III and subsequently quantitated, for example, by comparison to known reference standards. As demonstrated herein, MTX was accurately detected using reverse phase chromatography on a high performance liquid chromatography system. As a non-limiting example, chromatographic analysis can include passing an MTX containing sample through a C18 reverse phase column in a mobile phase consisting of a linear gradient from 2% acetonitrile/98% mobile phase A to 25% acetonitrile/75% mobile phase A, wherein mobile phase A is 10 mM ammonium acetate, pH 6.5.

The content of a solution that is used to detect MTX, or a photolytic product thereof, can be varied, for example, with respect to pH or acetonitrile content. The pH at which MTX, or a photolytic product thereof, is detected in a method of the invention can be in the range of, for example, about pH 2 to 8 or in the range of about pH 4 to 7. In particular embodiments, MTX, or a photolytic product thereof, can be detected, for example, at pH 4, 4.5, 5, 5.5, 6, 6.5 or 7. The amount of acetonitrile present during detection of MTX, or a photolytic product thereof, can be in the range of, for example, about 0% to 20% or about 10% to 20%. In particular embodiments the amount of acetonitrile present can be, for example, 5%, 10%, 15% or 20%.

A reverse phase column useful for separating MTX from other cellular components can have, for example, dimensions of 25 cm×4.6 mm, as exemplified herein. Columns having larger or smaller diameters, lengths or both can also be used, for example, to accommodate larger or smaller sample size. Flow rates can vary, for example, from 0.2 to 2.5 ml/min. As demonstrated herein, the flow rate for the mobile phase can be, for example, 1 ml/min. However, the flow rate of the mobile phase can be altered as desired. A slower flow rate, such as 0.8 ml/min, 0.5 ml/min or 0.2 ml/min, can be used, for example, with a smaller column or to increase MTX retention times. Alternatively a faster flow rate, such as 1.5 ml/min or 2.0 ml/min, can be used, for example, with a larger column or to decrease MTX retention times.

A level of MTX in a sample also can be detected in a method of the invention based on other properties of MTX including, for example, ultraviolet or visible light absorption properties, fluorescence, electrochemical properties, or mass. Methods for detection of MTX based on these properties are known in the art as described, for example, in Rubino, supra, 2001. As non-limiting examples, a level of MTXPG in a sample can be determined by efficiently converting MTXPGs to MTX under conditions suitable for efficient conversion and detecting the resulting MTX with UV/Vis absorption spectroscopy, fluorimetry, electrochemical detection, or mass spectrometry. Those skilled in the art will know or be able to determine an appropriate means for detecting methotrexate based on the accuracy and sensitivity desired and the presence of potentially interfering substances in the particular sample being analyzed.

The invention provides a method of optimizing therapeutic efficacy or reducing toxicity associated with methotrexate therapy administered to an individual. The method includes the steps of: (a) converting methotrexate polyglutamates to MTX in a cellular extract from an individual under conditions suitable for efficient conversion of MTXPGs to MTX; and (b) determining a level of MTX in the cellular extract, the level of MTX correlating with a level of MTXPGs, thereby determining a level of MTXPGs in the cellular extract, wherein a drug or dosage subsequently administered to the individual is selected based on the level of MTXPGs.

Intracellular levels of methotrexate polyglutamates can be associated with efficacy, with higher levels associated with toxicity. By determining the intracellular level of methotrexate polyglutamates, the methods of the invention can be useful for adjusting the amount or frequency of methotrexate therapy in order that the methotrexate polyglutamates are within the therapeutic range and do not exceed this range, thereby producing undesirable toxic side effects. Any of a variety of types of cellular extracts can be useful in a method of the invention for optimizing therapeutic efficacy or reducing toxicity associated with methotrexate therapy. Cell extracts can be prepared from any cell or tissue that is indicative of the efficacy or toxicity of methotrexate therapy such as a diseased cell or tissue, a target cell for MTX therapy or a cell that is representative of the amount of drug in diseased cells. As used herein, the term "target cell for MTX therapy" means a cell for which uptake of MTX is desired to treat a disease or condition. As non-limiting examples, cell extracts can be prepared from red blood cells, leukocytes, neutrophils, cancer cells, and tissue biopsies.

A method of the invention for optimizing therapeutic efficacy or reducing toxicity associated with methotrexate therapy can further include altering the methotrexate dosage subsequently administered to the individual based on the determined level of methotrexate polyglutamates. Where the determined level of MTXPGs is below a therapeutic range, the dose or frequency of methotrexate can be increased. Where the determined level of MTXPGs is above a therapeutic range, the dose or frequency of methotrexate can be reduced to avoid toxicity. A therapeutic range can be determined from dose-response information for a particular disease or condition and, if desired, for the age, gender and medical condition of the individual being treated. As an example, a level of MTXPG determined in a red blood cellular extract can be compared to dose-response information correlating red blood cell methotrexate polyglutamate levels with reduction of an arthritis symptoms. Dose-response information also can be obtained using well known clinical procedures relevant to the particular pathological condition.

In a particular embodiment of the invention, a cellular extract useful in a method of the invention for optimizing therapeutic efficacy or reducing toxicity associated with MTX therapy can be obtained from a non-target cell for MTX therapy. As used herein, the term "non-target cell for MTX therapy" means a cell for which uptake of MTX is not desired. Such a non-target cell can be a normal cell that is sensitive to levels of MTX or that is disposed to take up MTX that is administered by a particular route. Determining a MTXPG level in a cellular extract from a non-target cell also can be useful to determine toxicity of MTX therapy.

Methotrexate therapy can cause a variety of unwanted adverse effects that mimic folate deficiency including, for example, gastrointestinal intolerance, stomatitis, alopecia and cytopenia. Many adverse effects of methotrexate therapy are dose dependent and can be alleviated by administration of compensatory doses of folate. Accordingly, a method of the invention for optimizing therapeutic efficacy or reducing toxicity associated with methotrexate therapy can further include, if desired, altering the dose of folate, or a derivative thereof, subsequently administered to the individual based on the determined level of intracellular methotrexate polyglutamates.

The invention further provides an isolated deglutamated composition which is characterized as (a) present in a red blood cell extract following deglutamation; (b) having a retention time of about 12 minutes in a mobile phase consisting of a 15-minute linear gradient from 2% acetonitrile/98% mobile phase A to 25% acetonitrile/75% mobile phase A at a flow rate of 1 ml/min through a Terra MS C18 reverse phase column, which has dimensions of 25 cm×4.6 mm and a particle size of 5 micrometers, and where the mobile phase A contains 10 mM ammonium acetate, pH 6.5, and 0.06% hydrogen peroxide in water; and (c) having a fluorescence excitation spectrum with peaks at 299 nm and 402 nm in water and a fluorescence emission spectra with a peak at 460 nm in water. The endogenous compound can be further characterized as being photostable to irradiation with a 254 nm low pressure mercury ultraviolet lamp for 3 seconds, wherein following irradiation with 254 nm for 3 seconds the fluorescence excitation spectrum of the isolated deglutamated composition has peaks at 299 nm and 402 nm in water and the isolated deglutamated composition emits fluorescence at 464 nm in water. The endogenous compound can further be characterized, for example, as having a fluorescence emission peak at 460 nm in water.

The present invention further provides an isolated composition produced by: (a) converting polyglutamated compounds in a red blood cellular extract to produce deglutamated RBC compounds; (b) fractionating the deglutamated RBC compounds under conditions comprising passage of a mobile phase consisting of a 15-minute linear gradient from 2% acetonitrile/98% mobile phase A to 25% acetonitrile/75% mobile phase A at a flow rate of 1 ml/min through a Terra MS C18 reverse phase column, which has dimensions of 25 cm×4.6 mm and a particle size of 5 micrometers, and where the mobile phase A includes 10 mM ammonium acetate, pH 6.5 and 0.06% hydrogen peroxide in water; and (c) isolating a compound that elutes in a peak at 12 minutes, where the peak is detectable by emission at 464 nm upon excitation with radiation at 400 nm.

The invention also provides an isolated deglutamated composition, such as the endogenous compound described in Example IV, together with a pharmaceutically acceptable carrier. An isolated deglutamated composition of the invention can be, for example, a folate derivative; in this case, a pharmaceutical composition containing the derivative can be useful as a surrogate for folate in any of a variety of applications. Such a pharmaceutical composition can be useful, for example, in a method of reducing toxicity associated with methotrexate therapy. Thus, the present invention also provides a method of reducing toxicity associated with methotrexate therapy by administering to an individual treated with methotrexate therapy an effective dose of a pharmaceutical composition of the invention.

Any of a variety of pharmaceutical compositions are encompassed by the invention. As one example, a deglutamated composition can be administered as a solution or suspension together with a pharmaceutically acceptable carrier. Such a pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester. Pharmaceutically acceptable carriers can be sterile or substantially free from contaminating particles and organisms. A composition of the invention that includes a pharmaceutically acceptable carrier can be of sufficient purity and quality for use in humans. A pharmaceutical composition of the invention containing a deglutamated compound can optionally include methotrexate.

A pharmaceutical composition of the invention can be formulated for parenteral administration such as subcutaneous, intraperitoneal, intramuscular, intravenous, intradermal, intracranial, intratracheal, and epidural administration. A pharmaceutical composition of the invention also can be formulated for oral, topical (including buccal and sublingual), rectal, ophthalmic, nasal, intrauterine or vaginal administration. A pharmaceutical composition of the invention can be presented in unit dosage form and can be prepared by pharmaceutical techniques well known to those skilled in the art. Such techniques include the step of bringing into association the active ingredient and a pharmaceutical carrier or excipient.

Formulations suitable for parenteral administration include aqueous and non-aqueous sterile injectable solutions including any of the pharmaceutically acceptable carriers described above. The solutions can additionally contain, for example, one or more anti-oxidants, buffers, bacteriostats or solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

A pharmaceutically acceptable carrier can additionally contain any of a variety of physiologically acceptable compounds that act, for example, to stabilize the deglutamated compound. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; and other stabilizers or excipients.

A variety of routes of administration can be useful for delivering a pharmaceutical composition of the invention. Such routes include those described previously and will depend, in part, on the particular therapeutic need and formulation. One skilled in the art understands that an effective amount of the deglutamated compound is included in the pharmaceutical composition and depends on the pathological condition to be treated and the specific physical characteristics of the individual affected with the disease. Those skilled in the art will know or can determine a specific regime of administration which is effective for a particular application using the teachings and guidance provided herein together with diagnostic and clinical criteria known within the field of art of the particular pathological condition.

The invention further provides a kit including the endogenous deglutamated compound described in Example IV. In one embodiment, the kit further includes methotrexate. Those skilled in the art can readily incorporate a composition of the invention into kit form in combination with appropriate buffers and solutions for the practice of one or more of the methods disclosed herein.

A kit can include packaging material that houses the contents of the kit. The packaging material is constructed by well known methods, preferably to provide a sterile, contaminant-free environment. The packaging materials employed herein in relation to a kit or diagnostic system can be any acceptable material that is customarily utilized in small molecule-based therapeutic or diagnostic systems. A package can be any solid matrix or material such as glass, plastic, paper, foil, and the like, capable of holding within fixed limits a compound of the present invention. Thus, for example, a package can be a glass vial or microtiter plate used to contain microgram or milligram quantities of the endogenous deglutamated compound disclosed herein in Example IV.

The packaging material can include a label which indicates that the compositions can be used for reducing toxicity associated with methotrexate therapy, for determining an intracellular level of methotrexate, or for optimizing methotrexate therapy. In addition, the packaging material can include instructions indicating how the materials within the kit are employed. Such instructions will be in accordance with the description set forth herein for performing the methods. The instructions will typically include a tangible expression describing the concentration of the compound or at least one therapeutic or diagnostic method parameter including, without limitation, the relative amounts of the compound and methotrexate or some other component to be admixed, maintenance time periods for components of the kit, recommended temperature for storage or use, buffer conditions, and the like.

As further disclosed herein, intracellular levels of a deglutamated composition of the invention can be determined and used to calculated the intracellular level of methotrexate. Thus, the present invention provides a method for determining an intracellular level of methotrexate, by deglutamating a cellular extract to produce a deglutamated composition of the invention; and determining the level of deglutamated composition, where the level of the deglutamated composition can be correlated with the intracellular level of methotrexate. In one embodiment, the cellular extract is a red blood cellular extract.

The present invention further provides a method of optimizing therapeutic efficacy or reducing toxicity associated with methotrexate therapy administered to an individual by deglutamating compounds in a cellular extract from the individual; and determining a level of a deglutamated composition of the invention in the cellular extract, where a drug or dosage subsequently administered to the individual is selected based on the level of the deglutamated composition. The level of methotrexate can optionally also be determined in the cellular extract; in this case, a drug or dosage subsequently administered to the individual is selected based on the ratio of the level of methotrexate to the level of the deglutamated composition.

The following examples are intended to illustrate but not limit the present invention.

EXAMPLE I

Quantification of Methotrexate by Fluorimetric Detection of Methotrexate-Photolytic Products This example describes quantification of methotrexate using high performance liquid chromatography (HPLC) and post-column photolysis followed by fluorometric detection of photolytic products.

The MTX detection system was based on an HPLC system (Agilent 1100 HPLC chemstation system) equipped with a C18 reversed phase column (25 cm×4.6 mm X Terra MS C18, 5 micrometer particle size; Waters, Milford, Mass.), a post-column photochemical reactor unit (Aura Industries; New York, N.Y.) and a post-reactor unit fluorometer detector. The system also included a C18 pre-column that was changed every 200 injections.

Samples containing 20 to 1000 nmol/L MTX (Sigma, St. Louis, USA) in RBC extracts were run in the HPLC system at a flow rate of 1 ml/min, with a 15-minute linear gradient from 2% acetonitrile/98% mobile phase A (10 mM ammonium acetate, pH 6.5, unless otherwise indicated and 0.2% hydrogen peroxide in water) to 25% acetonitrile/75% mobile phase A, unless otherwise indicated. After 15 minutes, mobile phase was returned to 100% mobile phase A and the column was re-equilibrated for 5 minutes. The samples were maintained at 4° C. and injected every 20 minutes with an autoinjector.

Eluate from the column passed through the photochemical reactor unit in TEFLON™ tubing (1/16 inch outer diameter, 0.25 mm inner diameter, 8 meter length) that was connected on-line after the column and before the fluorometer detector and assembled as a knitted coil. The knitted coil was extended lengthwise through the photochemical reactor unit which also housed an elongated 254 nm low pressure mercury ultraviolet lamp (Aura Industries; New York, N.Y.). The time of irradiation of MTX in the photochemical reactor was 24 seconds. Irradiation for less than 24 seconds was achieved by masking all but a portion of the elongated lamp with foil such that only a portion of the knitted coil was irradiated. In particular, the lamp was masked such that only 1 meter of the coil was irradiated with the lamp which at a flow rate of 1 ml/min corresponded to 3 seconds irradiation. Methotrexate photolytic products were measured at an excitation wavelength set at 400 nm and an emission wavelength at 470 nm, unless otherwise indicated. Chromatograms were acquired and analyzed on a Hewlett-Packard Vector XA computer. The retention times described herein for the above-described HPLC system were measured from the time of injection to time of detection at the post-reactor unit fluorometer detector.

As shown in FIG. 2C, HPLC chromatography with in line photolysis under conditions that formed methotrexate photolytic product A, and fluorescence detection at an excitation wavelength of 400 nm and emission wavelength at 464 nm produced a single peak having a retention time of about 12.4 minutes. The limit of detection, defined as three times the signal-to-noise ratio, was 5 nmol/L for MTX. The analytical column demonstrated no deterioration of its performance after up to 1000 injections.

Two methotrexate photolytic products were obtained from the post-column derivatization. Product A was formed from the equivalent of a 3-second irradiation and exhibited an excitation spectrum with a wavelength maximum at 274 nm and a smaller peak with a maximum at 380 nm and an emission spectrum with wavelength maximum at 464 nm. FIG. 2D shows the fluorescence excitation and emission spectra for product A of the peak eluting at 12.42 minutes in two separate HPLC separations under conditions similar to those described for the chromatogram of FIG. 2C. Product B was formed following irradiation corresponding to 24 seconds using an 8 meter knitted reactor coil. Product B had maximum excitation at 370 nm and maximum emission at 417 nm.

The effect of pH on MTX detection was analyzed using the MTX detection system described above except that the mobile phase was isocratic and consisted of 10 mM ammonium acetate, 0.2% hydrogen peroxide in water, 10% acetonitrile and a different pH from 4.0 to 7.0. As shown in FIG. 2A, when detection was based on conversion to photolytic product A, increasing pH resulted in an increase in the peak area for MTX. However, the peak area was relatively unchanged at different pH values in this range, when detection was based on conversion to photolytic product B. At pH greater than about 4.2, product A exhibited higher fluorescence intensity compared to product B.

The effect of acetonitrile on MTX detection was analyzed using the MTX detection system described above except that the mobile phase was isocratic and consisted of 10 mM ammonium acetate, pH 6.0, 0.2% hydrogen peroxide in water and different percentages of acetonitrile varying from 10 to 20%. As shown in FIG. 2B, when detection was based on conversion to photolytic product A, increasing percentages of acetonitrile resulted in a decrease in the peak area for MTX. However, the peak area was relatively unchanged at different acetonitrile percentages in this range, when detection was based on conversion to photolytic product B. In the range of acetonitrile tested, product A exhibited higher fluorescence intensity compared to product B.

These results indicate that pH and percentage acetonitrile of the mobile phase and the time of irradiation can be changed to modify the sensitivity of MTX detection. In particular, these results indicate that the sensitivity of detection of MTX photolytic product A can be changed by altering pH and acetonitrile concentration.

EXAMPLE II

Conversion of Methotrexate Polyglutamates to Methotrexate

This example describes efficient conversion of methotrexate polyglutamates (MTXPGs) to methotrexate (MTX) and further demonstrates quantitation of methotrexate polyglutamates in a cellular extract.

MTXPGs were enzymatically converted to MTX by incubation with RBC extract and plasma as follows. RBCs were isolated from healthy donors (Blood bank; San Diego, Calif.) Hemolysates were prepared having $0.88 \times 10^9$ RBC per 100 μl. For spiked samples, MTXPG (Schirks Laboratories; Jona, Switzerland) was added to RBC extracts at a final concentration of 1 μM (from stock solutions containing 100 μM MTXPG in 0.1 N potassium hydroxide). Reconstituted plasma was prepared from lyophilized plasma (Sigma, St. Louis, USA; Cat. No. P9523) and 100 μl was added to 50 μl of RBC extract, mixed for 30 seconds, and 100 μl of buffer containing 100 mM potassium phosphate pH 4.5 and 150 mM mercaptoethanol was added. Because the reconstituted plasma and RBC extract are strongly buffered at physiological pH, the mixture had a final pH of about 6.5. Samples were incubated for 12-14 hours, unless otherwise indicated, in the dark at 37° C. After incubation 30 μl of 70% perchloric acid was added to the mixture, vortexed for 15 seconds and centrifuged for 10 minutes. A total volume of 80 μl was injected onto the HPLC system for analysis using the MTX detection system described in Example I.

Figure 3:
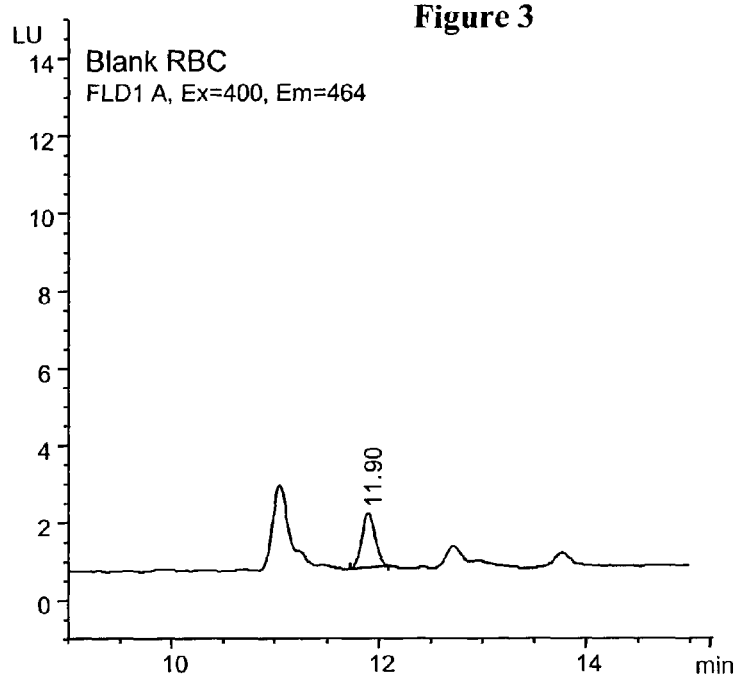
FIG. 3 shows typical chromatograms of red blood cell extracts. (A) A typical chromatogram of a deglutamated red blood cell extract following photolysis; (B) A typical chromatogram of a deglutamated, $MTXPG_{2-7}$-spiked red blood cell extract following photolysis; and (C) Fluorescence excitation spectrum of photolytic product A produced from the peak eluting at 12.5 minutes in the chromatogram of part B (indicated as "RBC") overlayed with excitation spectrum for photolytic product A produced from a methotrexate standard in water (indicated as "water").
Figure 3:
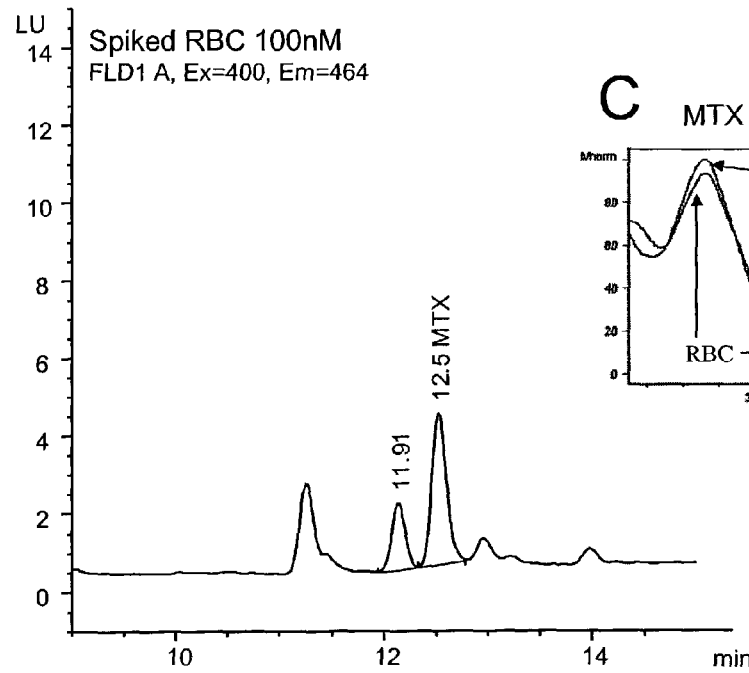
Figure 3:
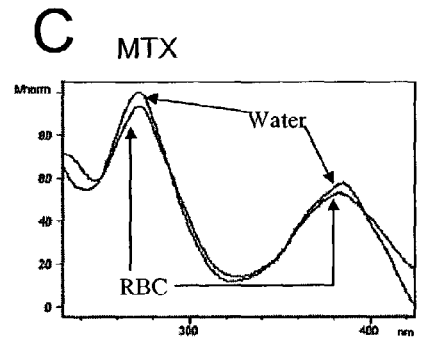

FIG. 3 shows typical chromatograms of an RBC extract blank (Panel A) and an RBC extract spiked with $MTXPG_{2-7}$ (Panel B, 100 nmol/L RBC) under the above-described conditions for enzymatic conversion to MTX. Although the maximum excitation wavelength for the methotrexate photolytic product was 274 nm, excitation wavelength was set at 400 nm to avoid interfering signals observed in the RBC extract blank. As shown in FIG. 3C, the excitation spectrum for the MTX photolytic product from the RBC extract that eluted at 12.5 minutes in the chromatogram shown in FIG. 3B was similar to the excitation spectrum for the photolytic product obtained from an MTX standard, measured in water. The overlap in the excitation spectra confirm that the 12.5 minute peak is MTX.

Standard curves demonstrated a linear relationship between peak area and concentration with correlation coefficients >0.995 for MTX, and for MTX formed after enzymatic conversion of $MTXPG_2$ (MTXPG having 2 glutamates) or $MTXPG_{2-7}$ (equimolar mixture of $MTXPG_2$, $MTXPG_3$, $MTXPG_4$, $MTXPG_5$, $MTXPG_6$, and $MTXPG_7$). Spiked standards were assayed in duplicate. Standard curves were fit by linear regression using peak areas versus concentrations. Equations describing the standard curves were: MTX, y=0.401x+0.281; MTX after enzymatic conversion of $MTXPG_2$, y=0.383x+0.115; and MTX after enzymatic conversion of $MTXPG_{2-7}$, y=0.391x−0.122 where y=peak area and x=spiked concentration.

Figure 4:
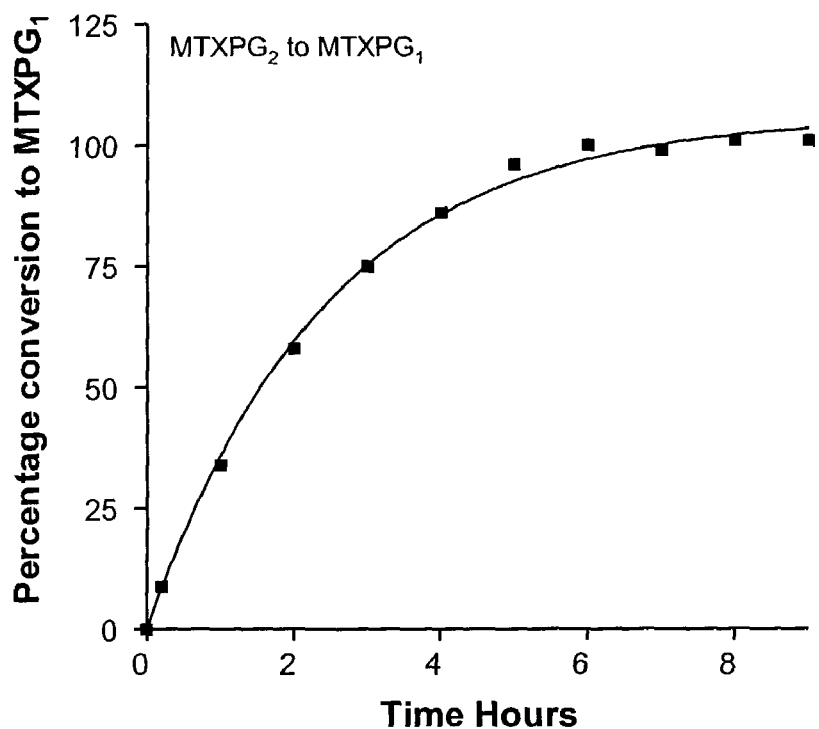
FIG. 4 shows the conversion results obtained for various methotrexate polyglutamates. (A) Timecourse of conversion of $MTXPG_2$ to MTX. (B) Timecourse of conversion of $MTXPG_{2-7}$ to MTX.
Figure 4:
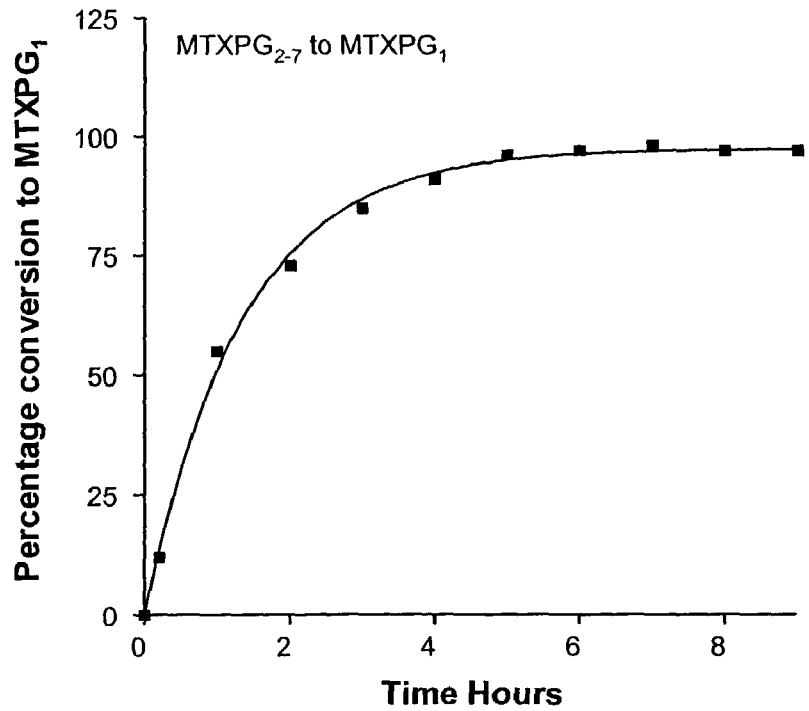

As shown in FIG. 4, $MTXPG_2$ (Panel A) and $MTXPG_{2-7}$ (Panel B) were completely converted to MTX after an 8 hour incubation at 37° C., in the dark, at concentration of 1000 nmol/L RBC and the conversion was largely complete by 4 hours. The percent conversion of MTXPG to MTX was determined by comparing the peak area of MTX formed during the enzymatic conversion at different times with the peak area of MTX spiked in the red blood cells at the same concentration.

The intra-day accuracy and inter-day accuracy for quantitation of MTX and MTXPGs are shown in Table I. RBC extracts were incubated with 20, 100 or 500 nmol/L of MTX, $MTXPG_2$ or $MTXPG_{2-7}$ (Target concentrations; see Table I), and the observed concentration of MTX was determined by the HPLC method described in Example I. For the intra-day accuracy assessment, the mean observed MTX concentration was determined for 10 spiked replicates at each target concentration (see Table I). The mean observed MTX concentrations for inter-day accuracy assessment were based on three replicates from five different days (Table 1). Accuracy was calculated as the percentage error of the mean observed MTX concentration from the target concentration value for each set of spiked samples (mean observed concentration/target concentration×100%). Precision was determined by the relative standard deviation (RSD).

TABLE I

| Standard | Target conc. nmol/L | Intra-day (n = 10) | | | Inter-day (n = 5) | | |
|---|---|---|---|---|---|---|---|
| | | Mean observed $MTXPG_1$ conc. nmol/L | RSD % | Mean accuracy of target value (%) | Mean observed $MTXPG_1$ conc. nmol/L | RSD % | Mean accuracy of target value (%) |
| $MTXPG_1$ | 50.0 | 45.0 | 4.8 | 90.0 | 48.9 | 8.4 | 97.9 |
| | 250.0 | 250.2 | 3.8 | 100.1 | 260.8 | 3.8 | 104.3 |
| | 500.0 | 504.2 | 4.1 | 100.8 | 517.3 | 2.3 | 103.5 |
| $MTXPG_2$ | 50.0 | 48.2 | 1.8 | 96.4 | 48.8 | 6.8 | 97.7 |
| | 250.0 | 231.1 | 4.2 | 92.5 | 238.5 | 2.7 | 95.4 |
| | 500.0 | 473.2 | 3.6 | 94.6 | 490.8 | 4.2 | 98.2 |
| $MTXPG_{2-7}$ | 50.0 | 45.4 | 4.7 | 90.7 | 47.0 | 4.3 | 94.1 |
| | 250.0 | 244.5 | 3.3 | 97.8 | 245.6 | 4.1 | 98.2 |
| | 500.0 | 473.2 | 2.3 | 94.6 | 492.8 | 6.1 | 98.6 |

Figure 5:
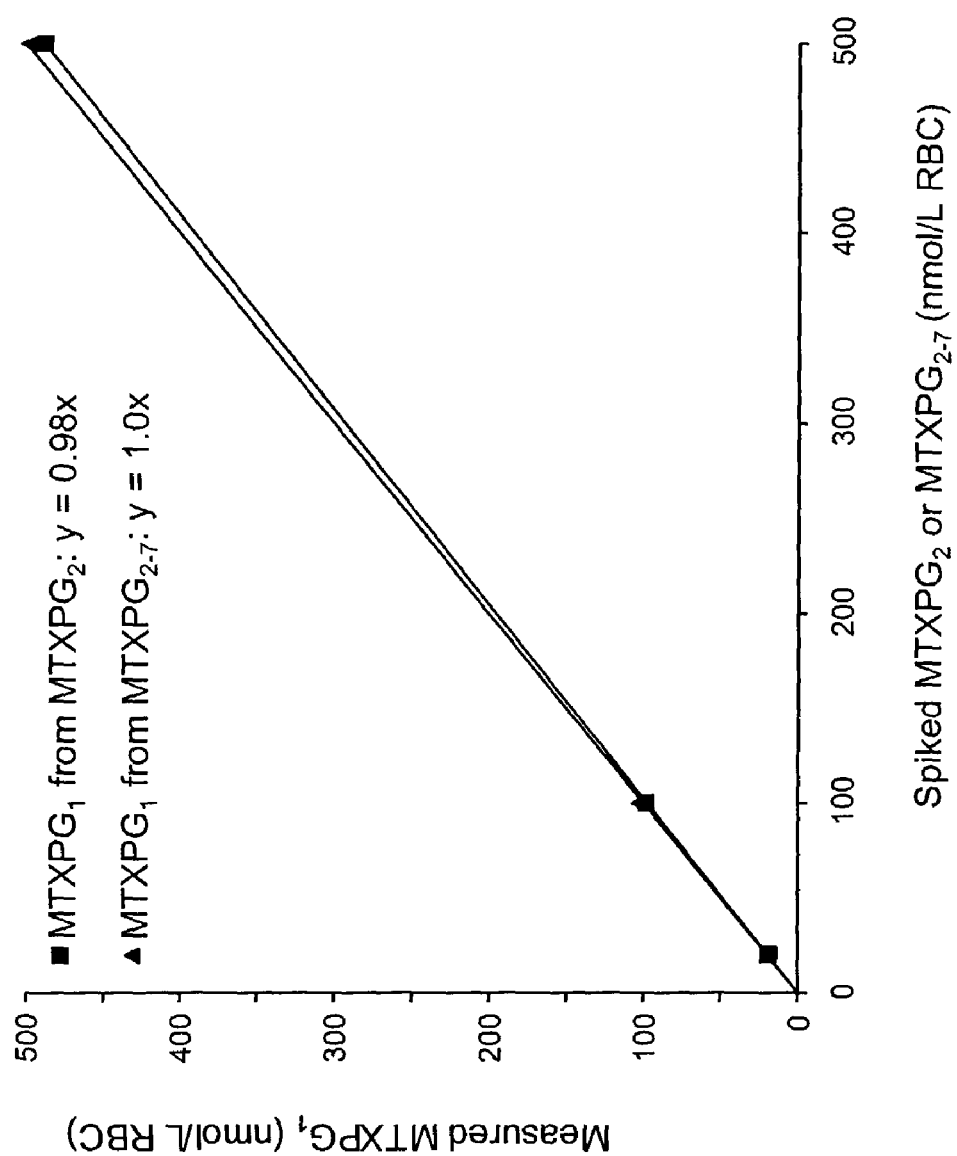
FIG. 5 shows a plot of detected MTX concentration versus the concentration of $MTXPG_2$ or $MTXPG_{2-7}$ added to a red blood cell sample prior to deglutamation. MTX from samples with $MTXPG_2$ is shown as squares. MTX from samples with $MTXPG_{2-7}$ is shown as triangles.

Highly efficient conversion of $MTXPG_2$ and $MTXPG_{2-7}$, respectively, to MTX was demonstrated by the accuracies of greater than 95% and a coefficient of variation less than 6% for all target concentrations as shown in Table I. Furthermore, as shown in FIG. 5, the plots of observed MTX concentration versus the concentration of spiked $MTXPG_2$ or $MTXPG_{2-7}$ had slopes of 0.98 and 1.0 respectively, demonstrating that the method was accurate and converted greater than 95% methotrexate polyglutamates to methotrexate. The lower limit of quantification of MTXPG by conversion to MTX and analysis on the MTX detection system was 10 nmol/L MTXPG.

These results demonstrate that MTXPG can be efficiently converted to MTX in RBC extract samples using plasma as a source of gamma glutamyl hydrolase. The results further demonstrate that methotrexate polyglutamates can be accurately and quantitatively detected in RBC extracts by converting the MTXPGs to MTX and quantitating the amount of MTX by fluorescent detection of a MTX photolytic product.

EXAMPLE III

Monitoring Methotrexate Polyglutamate Levels in Patients Receiving Low-Dose Methotrexate Therapy Methotrexate requires intracellular activation to methotrexate polyglutamate to exert anti-arthritic effects. This example describes a method for quantitating the levels of intracellular methotrexate polyglutamates in the RBCs of a patient following administration of low-dose MTX therapy.

Blood samples (5 ml) from polyarthritis patients receiving low-dose MTX were collected after written informed consent. The patients had received a median of 15 mg MTX (range 2.5 mg to 40 mg per week) for at least three months. Blood samples were centrifuged for 10 minutes to separate plasma and buffy coat from RBCs. After washing the RBC pellet with 2 volumes of saline, RBC count was determined with a Beckman Coulter Onyx Counter; RBCs were subsequently stored at −70° C. until analysis. Results were normalized to $10^9$ red blood cells. Patient results were expressed as average ±SEM (range).

MTXPG concentrations were determined using the methods described in Example II except that RBC extracts were not spiked with MTXPG. MTXPG concentrations were calculated by subtracting MTX concentrations measured after enzymatic treatment with MTX concentrations measured in a corresponding sample not subject to enzymatic treatment. To quantify MTX concentrations without enzymatic treatment, a second 100 µl aliquot of patient RBC extract was obtained but not treated with plasma or buffer. Rather, 200 µl water was added to the RBC extract prior to immediate deproteinization with 30 µl 70% perchloric acid as described above.

An exemplary determination of MTXPG concentration in the red blood cells of a patient on 2.5 mg per week MTX therapy follows. A total of $0.88 \times 10^9$ RBC cells were obtained from the patient and analyzed and resulted in the chromatogram shown in FIG. 6A. The fluorescence excitation spectrum of photolytic product A produced from the peak eluting at 12.42 minutes in the chromatogram of FIG. 6A was similar to the excitation spectrum for methotrexate's photolytic product in water as shown in FIG. 6B. The overlap in the excitation spectra confirm that the 12.42 minute peak is MTX.

The concentration of MTXPG in the sample was determined to be 7.9 pmol $MTXPG/10^9$ cells by subtracting the MTX concentration prior to enzymatic conversion, which was 16.5 pmol $MTXPG/10^9$ cells, from MTX after enzymatic conversion, which was 28.6 pmol $MTXPG/10^9$ cells. Based on these results, it was determined that 27% of the total MTX in the patient's RBCs was present as a polyglutaminated derivative.

In 12 patients, total MTXPG ranged from 3.4 to 37.0 pmol $MTXPG/10^9$ cells with a median of 16.5 pmol $MTXPG/10^9$ cells. Prior to conversion, MTX concentration ranged from 1.9 to 30.0 pmol/$10^9$ cells. The percentage of MTXPG in the patients' RBCs ranged from 35% to 100% of total MTX with a median of 45%.

These results demonstrate an assay that is capable of detecting the amount of RBC intracellular MTX in a patient on low dose MTX therapy as well as the amount of this MTX that has been converted to the active MTXPG form.

EXAMPLE IV

A Compound Isolated from a Deglutamated Red Blood Cellular Extract

This example describes isolation and characterization of a compound isolated from red blood cells following deglutamation.

RBCs were isolated, hemolysates prepared and the hemolysates deglutamated by incubation with reconstituted plasma as described in Example II. Deglutamated samples were injected onto the HPLC system for analysis using the MTX detection system described in Example I.

Figure 6:
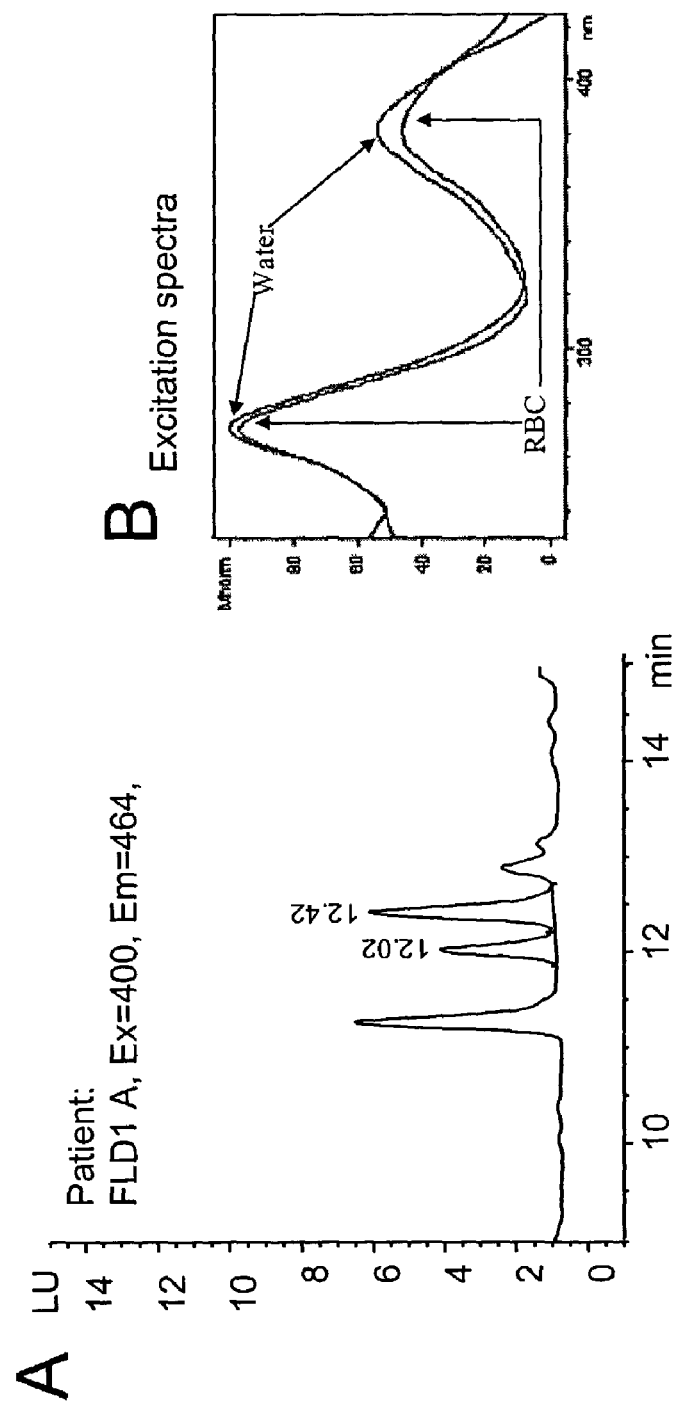
FIG. 6 shows characterization of a red blood cell patient sample. (A) Chromatogram of a deglutamated RBC extract from a patient having received low-dose MTX therapy. (B) Fluorescence excitation spectrum of photolytic product A produced from the peak eluting at 12.42 minutes in the chromatogram of part A (indicated as "RBC") overlayed with excitation spectrum for photolytic product A produced from a methotrexate standard in water (indicated as "water").

As shown in FIG. 3A, an endogenous peak having a retention time of 11.90 minutes was detected in the deglutamated RBC extract. The endogenous peak had a retention time of 11.91 minutes in a deglutamated RBC extract that had been spiked with MXTPG and was resolved from the MTX peak, which had a retention time of 12.5 minutes (FIG. 3B). In a deglutamated RBC extract from a patient undergoing methotrexate therapy, the endogenous peak had a retention time of 12.02 minutes and was again resolved from the MTX peak, which had a retention time of 12.42 minutes (FIG. 6). In both the MTXPG spiked sample and patient sample, the resolution was sufficient to allow the endogenous peak to be integrated for quantitative comparison between samples. The endogenous peak had retention times that were about 0.6 to 0.4 minutes less than the retention times for MTX.

Figure 7:
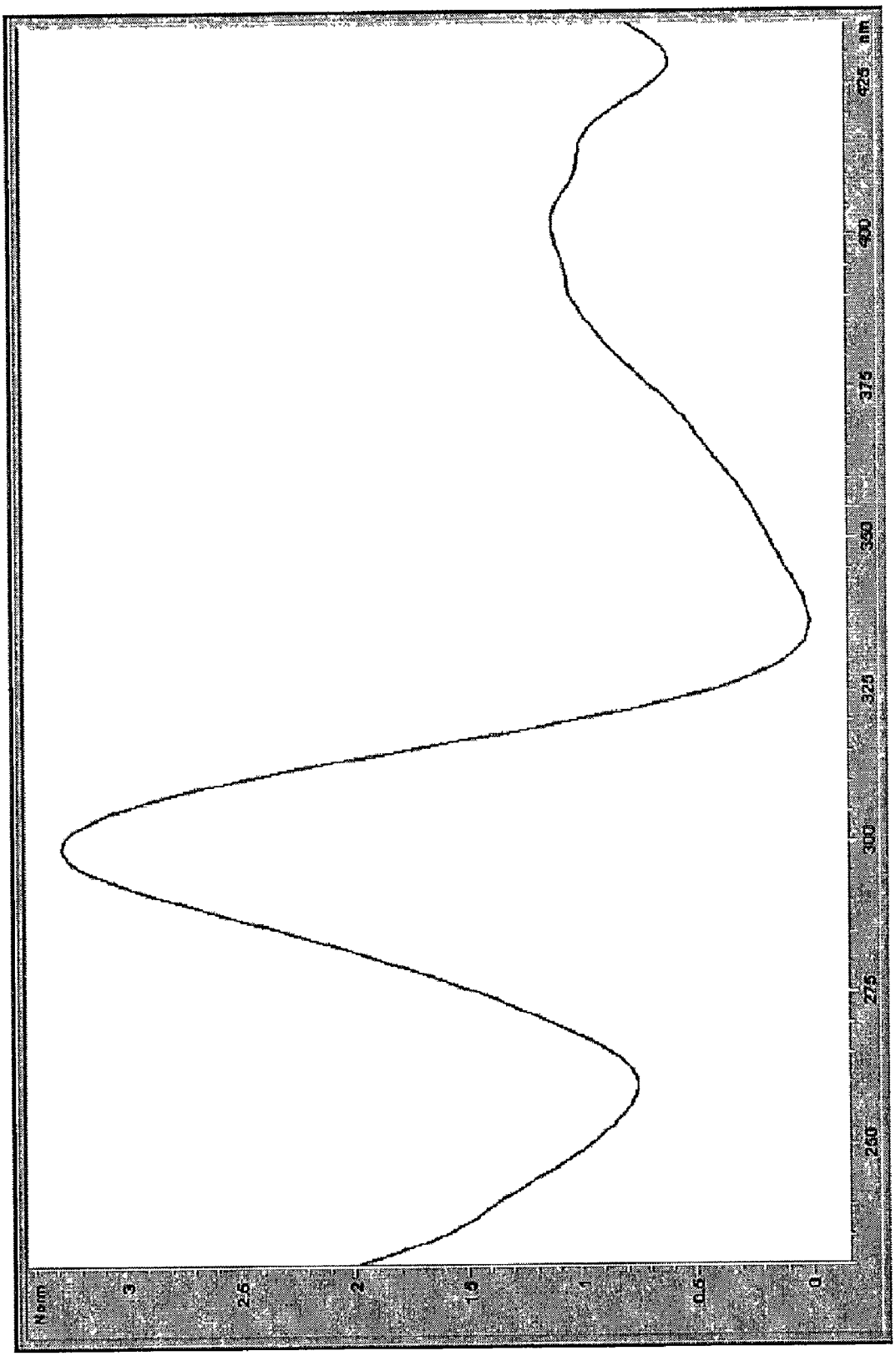
FIG. 7 shows a fluorescence excitation spectrum obtained for the eluate at 12.02 minutes in the chromatograph of FIG. 6A.

A fluorescence excitation spectrum was obtained for the material eluting with the endogenous peak by detecting emission at 464 nm for the HPLC column eluate having a retention time of 12.02 minutes. As shown in FIG. 7, the excitation spectrum had peak maxima at about 299 nm and 402 nm and minima at about 259 nm, 336 nm and 429 nm.

The excitation spectrum of the endogenous peak shown in FIG. 7 was obtained following 3 second photolysis under the conditions set forth in Example I. Also shown in FIG. 7 is the excitation spectrum obtained for the endogenous peak under similar HPLC conditions except that the sample was not irradiated prior to detection. The spectra for the endogenous peak with and without photolysis were similar, indicating that the endogenous compound isolated from deglutamated red blood cellular extracts is photostable to UV irradiation for at least 3 seconds in the presence of peroxide.

The endogenous compound that is present in the endogenous peak is obtained by isolating from the column eluate the fraction corresponding in retention time to the endogenous peak. The presence of the compound in the isolated fraction is confirmed by analysis of a portion of the fraction. This portion is analyzed by reinjection onto the HPLC system using the post-column photolysis and fluorescence detection system described in Example I and the presence of the compound identified by elution at the appropriate time.

The endogenous compound is characterized by co-injection with known folates in the HPLC system or other analytical chromatography system. A known folate that coelutes with the endogenous compound is identified as potentially having similar structure. Further characterization of the endogenous compound is based on the rate at which it is produced by GGH compared to the rate at which a known polyglutamated folate is converted to a monoglutamated folate or the photostability of the endogenous compound compared to photostability of a known folate. Similarity in the reaction rates, photostability or both also identifies the endogenous compound as having a structure that is similar to the known folate.

The molecular weight of the endogenous compound is determined by mass spectrometry using methods known in the art. Further structural characterization is carried out by nuclear magnetic resonance spectroscopy using methods known in the art as applied to analysis of methotrexate and other folates.

Throughout this application various patent and non-patent publications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the spirit of the invention. Accordingly, the invention is limited only by the claims.

What is claimed is:

1. A method for determining a level of methotrexate polyglutamates (MTXPGs) in a cellular lysate, comprising the steps of:
    (a) converting said MTXPGs to methotrexate (MTX) in said cellular lysate with gamma glutamyl hydrolase under conditions suitable for efficient conversion of MTXPGs to MTX;
    (b) determining said level of MTXPGs by UV irradiating and chromatographing said MTX under conditions effective to produce a fluorescent MTX photolytic product, having an excitation wavelength in the range of 250 nm to 290 nm, wherein the fluorescence excitation maxima of said photoproduct is 274 nm in water;
    (c) detecting fluorescence at an emission wavelength in the range of 440 nm to 500 nm, wherein the fluorescence emission maxima of said photoproduct is 464 nm in water; and
    (d) correlating the level of fluorescent MTX photolytic product with said level of MTXPGs in said cellular lysate by a standard curve.

2. The method of claim 1, wherein step (a) comprises contacting said cellular lysate with plasma comprising gamma glutamyl hydrolase.

3. The method of claim 1, wherein said cellular lysate is a fractionated cellular lysate based on the enrichment of MTX or polyglutamates thereof.

4. The method of claim 1 or claim 3, wherein said cellular lysate is a red blood cell lysate.

5. The method of claim 1 or claim 3, wherein said cellular lysate is a leukocyte lysate.

6. The method of claim 1 or claim 3, wherein said cellular lysate is a human cellular lysate.

7. The method of claim 6, wherein said cellular lysate is from an individual having an autoimmune disease.

8. The method of claim 7, wherein said cellular lysate is from an individual having arthritis.

9. The method of claim 7, wherein said cellular lysate is from an individual having a condition selected from the group consisting of rheumatoid arthritis, polyarthritis, systemic lupus erythematosus, and psoriasis.

10. The method of claim 6, wherein said cellular lysate is from an individual having cancer.

11. The method of claim 1, wherein said chromatographing comprises high performance liquid chromatography (HPLC).

12. The method of claim 1, wherein step (b) comprises contacting said MTX with radiation having a wavelength in the range of 225 nm to 275 nm to produce said photolytic product.

13. The method of claim 1, wherein step (c) comprises detecting fluorescence of said photolytic product at an excitation wavelength in the range of 260 nm to 280 nm.

14. The method of claim 1, wherein step (c) further comprises detecting fluorescence of said photolytic product at an excitation wavelength in the range of 360 nm to 410 nm.

15. A method of optimizing therapeutic efficacy or reducing toxicity associated with methotrexate (MTX) therapy administered to an individual, comprising the steps of:
    (a) converting methotrexate polyglutamates (MTXPGs) to MTX in a cellular lysate from said individual with gamma glutamyl hydrolase under conditions suitable for efficient conversion of MTXPGs to MTX;
    (b) determining said level of MTXPGs by UV irradiating and chromatographing said MTX under conditions effective to produce a fluorescent MTX photolytic product, having an excitation wavelength in the range of 250 nm to 290 nm, wherein the fluorescence excitation maxima of said photoproduct is 274 nm in water;

(c) detecting fluorescence at an emission wavelength in the range of 440 nm to 500 nm, wherein the fluorescence emission maxima of said photoproduct is 464 nm in water;

(d) correlating said level of fluorescent MTX photolytic product with said level of MTXPGs in said cellular lysate by a standard curve; and (e) selecting a drug or dosage that is based on the level of said correlated level of MTXPGs determined by step (d) for subsequent administration to said individual.

16. The method of claim 15, wherein said cellular lysate is obtained from a target cell for MTX therapy.

17. The method of claim 15, wherein said cellular lysate is obtained from a non-target cell for MTX therapy.

18. The method of claim 15, comprising reducing the dose of MTX administered to said individual.

19. The method of claim 15, comprising increasing the dose of MTX administered to said individual.

20. The method of claim 15, wherein the drug is folic acid, or a derivative thereof.

21. The method of claim 1, wherein said conditions of step (a) comprise a pH of at least 4.

22. The method of claim 21, wherein said conditions of step (a) comprise a pH in the range of 6 to 7.

23. The method of claim 1, wherein step (b) comprises irradiating said MTX for 0.5 to 60 seconds.

24. The method of claim 23, wherein step (b) comprises irradiating said MTX for 0.5 to 15 seconds.

25. The method of claim 1, wherein said chromatographing occurs prior to said UV irradiating.

26. The method of claim 1, wherein step (b) comprises HPLC with an aqueous mobile phase having a pH of 2 to 8.

27. The method of claim 26, wherein said aqueous mobile phase has a pH of 4 to 7.

28. The method of claim 26, wherein said aqueous mobile phase has a pH of 6 to 7.

29. The method of claim 1, wherein step (b) comprises HPLC with an aqueous mobile phase having at most 20% acetonitrile.

30. The method of claim 29, wherein said aqueous mobile phase has at most 15% acetonitrile.

31. The method of claim 1, wherein step (b) comprises HPLC with an aqueous mobile phase having 0.05% to 1% $H_2O_2$.

32. The method of claim 31, wherein said aqueous mobile phase has 0.3% to 0.6% $H_2O_2$.

* * * * *

UNITED STATES PATENT AND TRADEMARK OFFICE
CERTIFICATE OF CORRECTION

| | |
|---|---|
| PATENT NO. | : 7,563,590 B2 |
| APPLICATION NO. | : 10/232760 |
| DATED | : July 21, 2009 |
| INVENTOR(S) | : Dervieux et al. |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 363 days.

Delete the phrase "by 363 days" and insert -- by 877 days --

Signed and Sealed this

Twenty-seventh Day of April, 2010

David J. Kappos
*Director of the United States Patent and Trademark Office*